US009603810B2

(12) United States Patent
Amsden et al.

(10) Patent No.: US 9,603,810 B2
(45) Date of Patent: Mar. 28, 2017

(54) NANOIMPRINTING OF SILK FIBROIN STRUCTURES FOR BIOMEDICAL AND BIOPHOTONIC APPLICATIONS

(71) Applicant: Tufts University, Medford, MA (US)

(72) Inventors: Jason J. Amsden, Durham, NC (US); David L. Kaplan, Concord, MA (US); Fiorenzo G. Omenetto, Lexington, MA (US)

(73) Assignee: TUFTS UNIVERSITY, Medford, MA (US)

( * ) Notice: Subject to any disclaimer, the term of this patent is extended or adjusted under 35 U.S.C. 154(b) by 0 days.

(21) Appl. No.: 14/265,781

(22) Filed: Apr. 30, 2014

(65) Prior Publication Data

US 2015/0272903 A1 Oct. 1, 2015

Related U.S. Application Data

(63) Continuation of application No. 13/201,380, filed as application No. PCT/US2010/024004 on Feb. 12, 2010, now Pat. No. 8,747,886.

(Continued)

(51) Int. Cl.
*A61K 41/00* (2006.01)
*A61K 47/42* (2006.01)
(Continued)

(52) U.S. Cl.
CPC ............. *A61K 9/7007* (2013.01); *A61K 9/70* (2013.01); *A61K 41/00* (2013.01); *A61K 47/42* (2013.01);
(Continued)

(58) Field of Classification Search
CPC .......... A61K 41/00; A61K 47/42; A61K 9/70; A61K 9/7007; B82Y 10/00; B82Y 20/00;
(Continued)

(56) References Cited

U.S. PATENT DOCUMENTS

| 4,676,640 A | 6/1987 | Briggs |
| 5,252,285 A | 10/1993 | Lock |

(Continued)

FOREIGN PATENT DOCUMENTS

| EP | 0245509 A1 | 11/1987 |
| EP | 1116987 A2 | 7/2001 |

(Continued)

OTHER PUBLICATIONS

Amsden, J.J. et al., Rapid nanoimprinting of silk fibroin films for biophotonic applications, Adv. Mater., 22(15):1746-9 (2010).

(Continued)

*Primary Examiner* — Ernst V Arnold
(74) *Attorney, Agent, or Firm* — Choate, Hall & Stewart, LLP

(57) ABSTRACT

The present invention provides for photonic nanoimprinted silk fibroin-based materials and methods for making same, comprising embossing silk fibroin-based films with photonic nanometer scale patterns. In addition, the invention provides for processes by which the silk fibroin-based films can be nanoimprinted at room temperature, by locally decreasing the glass transition temperature of the silk film. Such nanoimprinting process increases high throughput and improves potential for incorporation of silk-based photonics into biomedical and other optical devices.

15 Claims, 13 Drawing Sheets

Related U.S. Application Data

(60) Provisional application No. 61/151,866, filed on Feb. 12, 2009.

(51) Int. Cl.

| | | |
|---|---|---|
| *B82Y 10/00* | (2011.01) | |
| *A61K 9/70* | (2006.01) | |
| *B82Y 20/00* | (2011.01) | |
| *B82Y 30/00* | (2011.01) | |
| *B82Y 40/00* | (2011.01) | |
| *G01N 21/47* | (2006.01) | |
| *G01N 21/77* | (2006.01) | |
| *G02B 5/18* | (2006.01) | |
| *G02B 6/122* | (2006.01) | |
| *G02B 6/26* | (2006.01) | |
| *G03F 7/00* | (2006.01) | |
| *G02B 6/02* | (2006.01) | |

(52) U.S. Cl.
CPC .............. *B82Y 10/00* (2013.01); *B82Y 20/00* (2013.01); *B82Y 30/00* (2013.01); *B82Y 40/00* (2013.01); *G01N 21/4788* (2013.01); *G01N 21/774* (2013.01); *G02B 5/1809* (2013.01); *G02B 6/1225* (2013.01); *G02B 6/262* (2013.01); *G03F 7/0002* (2013.01); *G01N 2021/7776* (2013.01); *G02B 5/1847* (2013.01); *G02B 6/02061* (2013.01); *Y10T 428/24479* (2015.01)

(58) Field of Classification Search
CPC  B82Y 30/00; B82Y 40/00; G01N 2021/7776; G01N 21/4788; G01N 21/774; G02B 5/1809; G02B 5/1847; G02B 6/02061; G02B 6/1225; G02B 6/262; G03F 7/0002; Y10T 428/24479
See application file for complete search history.

(56) References Cited

U.S. PATENT DOCUMENTS

| | | |
|---|---|---|
| 5,427,096 A | 6/1995 | Bogusiewicz et al. |
| 5,512,218 A | 4/1996 | Gresser et al. |
| 6,134,045 A | 10/2000 | Jiang et al. |
| 6,150,491 A | 11/2000 | Akkara |
| 6,284,418 B1 | 9/2001 | Trantolo |
| 6,924,503 B2 | 8/2005 | Cheng et al. |
| 6,989,897 B2 | 1/2006 | Chan et al. |
| 6,992,325 B2 | 1/2006 | Huang |
| 7,223,609 B2 | 5/2007 | Anvar et al. |
| 8,005,526 B2 | 8/2011 | Martin et al. |
| 8,747,886 B2 | 6/2014 | Amsden et al. |
| 2001/0002417 A1 | 5/2001 | Akkara et al. |
| 2001/0003043 A1 | 6/2001 | Metspalu et al. |
| 2002/0028243 A1 | 3/2002 | Masters |
| 2003/0203366 A1 | 10/2003 | Lim et al. |
| 2003/0214057 A1 | 11/2003 | Huang |
| 2004/0001299 A1 | 1/2004 | van Haaster et al. |
| 2004/0029241 A1 | 2/2004 | Hahn et al. |
| 2004/0081384 A1 | 4/2004 | Datesman et al. |
| 2004/0229349 A1 | 11/2004 | Daridon |
| 2005/0008675 A1 | 1/2005 | Bhatia et al. |
| 2005/0151966 A1 | 7/2005 | Packirisamy et al. |
| 2005/0194365 A1 | 9/2005 | Li |
| 2005/0213868 A1 | 9/2005 | Cunningham |
| 2005/0217990 A1 | 10/2005 | Sibbett et al. |
| 2005/0276791 A1 | 12/2005 | Hansford et al. |
| 2006/0042822 A1 | 3/2006 | Azeyanagi et al. |
| 2006/0091571 A1 | 5/2006 | Akutsu et al. |
| 2006/0134606 A1 | 6/2006 | Montagu |
| 2006/0141617 A1 | 6/2006 | Desai et al. |
| 2006/0177479 A1 | 8/2006 | Giachelli et al. |
| 2006/0178655 A1 | 8/2006 | Santini et al. |
| 2006/0226575 A1 | 10/2006 | Maghribi et al. |
| 2006/0236436 A1 | 10/2006 | Li et al. |
| 2007/0007661 A1 | 1/2007 | Burgess et al. |
| 2007/0009968 A1 | 1/2007 | Cunningham et al. |
| 2007/0026064 A1 | 2/2007 | Yoder et al. |
| 2007/0031607 A1 | 2/2007 | Dubson et al. |
| 2007/0042505 A1 | 2/2007 | Israel et al. |
| 2007/0058254 A1 | 3/2007 | Kim |
| 2007/0073130 A1 | 3/2007 | Finch et al. |
| 2007/0178240 A1 | 8/2007 | Yamazaki et al. |
| 2007/0233208 A1 | 10/2007 | Kurtz et al. |
| 2008/0019925 A1 | 1/2008 | Begleiter |
| 2008/0038236 A1 | 2/2008 | Gimble et al. |
| 2008/0152281 A1 | 6/2008 | Lundquist et al. |
| 2008/0203431 A1 | 8/2008 | Garcia et al. |
| 2008/0239755 A1 | 10/2008 | Parker et al. |
| 2008/0288037 A1 | 11/2008 | Neysmith et al. |
| 2009/0028910 A1 | 1/2009 | DeSimone et al. |
| 2009/0208555 A1 | 8/2009 | Kuttler et al. |
| 2010/0028451 A1 | 2/2010 | Kaplan et al. |
| 2010/0063404 A1 | 3/2010 | Kaplan et al. |
| 2010/0120116 A1 | 5/2010 | Kaplan et al. |
| 2012/0034291 A1 | 2/2012 | Amsden et al. |

FOREIGN PATENT DOCUMENTS

| | | |
|---|---|---|
| EP | 1166987 A2 | 1/2002 |
| EP | 1467224 A1 | 10/2004 |
| JP | 60-142259 A | 7/1985 |
| JP | 60155129 A | 8/1985 |
| JP | 01280242 A | 11/1989 |
| JP | 02086799 A | 3/1990 |
| JP | H05-188031 A | 7/1993 |
| JP | 11042106 A | 2/1999 |
| JP | 2000-096490 A | 4/2000 |
| JP | 2000-143472 A | 5/2000 |
| JP | 2001-147301 A | 5/2001 |
| JP | 2001-280242 A | 10/2001 |
| JP | 2002-287377 A | 10/2002 |
| JP | 2003-195001 A | 7/2003 |
| JP | 2003-322729 A | 11/2003 |
| JP | 2004-162209 A | 6/2004 |
| JP | 2005-530983 A | 10/2005 |
| JP | 2006241450 A | 9/2006 |
| KR | 2006-0027113 A | 3/2006 |
| KR | 2007-0060822 A | 6/2007 |
| KR | 2008-0069553 A | 7/2008 |
| WO | WO-93/15244 A1 | 8/1993 |
| WO | WO-00/31752 A2 | 6/2000 |
| WO | WO-01/85637 A2 | 11/2001 |
| WO | WO-03/038033 A2 | 5/2003 |
| WO | WO-2004/000915 A2 | 12/2003 |
| WO | WO-2004/092250 A1 | 10/2004 |
| WO | WO-2005/012606 A2 | 2/2005 |
| WO | WO-2005/019503 A2 | 3/2005 |
| WO | WO-2006/020507 A1 | 2/2006 |
| WO | WO-2008/118211 A2 | 10/2008 |
| WO | WO-2008/127403 A2 | 10/2008 |
| WO | WO-2008/127404 A2 | 10/2008 |
| WO | WO-2008/127405 A2 | 10/2008 |
| WO | WO-2009/061823 A1 | 5/2009 |
| WO | WO-2010/059963 A2 | 5/2010 |

OTHER PUBLICATIONS

Bai, J. et al., Regenerated spider silk as a new biomaterial for MEMS, Biomed Microdevices, 8:317-323 (2006).

Chrisey, D.B. et al., Laser Deposition of Polymer and Biomaterial Films, Chem. Rev 103(2):553-576 (2003).

Extended European Search Report for EP 10770086.6, 4 pages (Dec. 11, 2014).

Fukuoka T. et al., Enzymatic Polymerization of Tyrosine Derivatives. Peroxidase- and Protease-Catalyzed Synthesis of Poly(tyrosine)s with Different Structures, Biomacromolecules 3(4):768-774 (2002).

International Preliminary Report on Patentability for PCT/US2007/083600, 6 pages (May 5, 2009).

(56) References Cited

OTHER PUBLICATIONS

International Preliminary Report on Patentability for PCT/US2007/083605, 10 pages (May 5, 2009).
International Preliminary Report on Patentability for PCT/US2007/083620, 6 pages (May 5, 2009).
International Preliminary Report on Patentability for PCT/US2007/083634, 6 pages (May 5, 2009).
International Preliminary Report on Patentability for PCT/US2007/083639, 6 pages (May 5, 2009).
International Preliminary Report on Patentability for PCT/US2007/083642, 6 pages (May 5, 2009).
International Preliminary Report on Patentability for PCT/US2007/083646, 10 pages (May 5, 2009).
International Preliminary Report on Patentability for PCT/US2008/082487, 10 pages (May 11, 2010).
International Preliminary Report on Patentability for PCT/US2009/047751, 5 pages (Dec. 18, 2010).
International Preliminary Report on Patentability for PCT/US2010/022701, 5 pages (Aug. 2, 2011).
International Preliminary Report on Patentability for PCT/US2010/024004, 6 pages (Aug. 16, 2011).
International Preliminary Report on Patentability for PCT/US2010/042585, 6 pages (Jan. 24, 2012).
International Preliminary Report on Patentability for PCT/US2010/047307, 5 pages (Mar. 6, 2012).
International Search Report for PCT/US2007/083600, 5 pages (Nov. 5, 2008).
International Search Report for PCT/US2007/083605, 6 pages (Dec. 15, 2008).
International Search Report for PCT/US2007/083620, 4 pages (Dec. 5, 2008).
International Search Report for PCT/US2007/083639, 5 pages (Dec. 12, 2008).
International Search Report for PCT/US2007/083642, 5 pages (Nov. 5, 2008).
International Search Report for PCT/US2007/083646, 6 pages (Dec. 15, 2008).
International Search Report for PCT/US2008/082487, 3 pages (Feb. 27, 2009).
International Search Report for PCT/US2009/047751, 3 pages (Feb. 2, 2010).
International Search Report for PCT/US2010/022701, 2 pages (Mar. 31, 2010).
International Search Report for PCT/US2010/024004, 5 pages (Nov. 26, 2010).
International Search Report for PCT/US2010/042585, 8 pages (May. 25, 2011).
International Search Report for PCT/US2010/047307, 3 pages (Apr. 28, 2011).
International Search Report for PCT/US2010/050468, 3 pages (Jan. 6, 2011).
International Search Report for PCT/US2011/028094, 4 pages (Jul. 14, 2011).
International Search Report for PCT/US2011/032195, 3 pages (Oct. 27, 2011).
International Search Report for PCT/US2011/041002, 4 pages (Feb. 29, 2012).
Jiang, W. et al, Silicon and Polymer Nanophotonic Devices Based on Photonic Crystals, Proceedings of the International Society of Optical Engineering, 6124(1):612410-1(2006).
Jin, H.J. et al., Water-Stable Silk Films with Reduced β-Sheet Content, Advanced Functional Materials, 15:1241-1247 (2005).
Kouba et al., Fabrication of Nanoimprint Stamps for Photonic Crystals, Journal of Physics: Conference Series, 34(1):897-903 (2006).
Lawrence, B.D. et al., Bioactive silk protein biomaterial systems for optical devices, Biomacromolecules, 9:1214-1220 (2008).
Min, B.M. et al., Regenerated Silk Fibroin Nanofibers: Water Vapor-Induced Structural Changes and Their Effects on the Behavior of Normal Human Cells, Macromol. Biosci., 6(4):285-292 (2006).
Minoura, N. et al., Attachment and Growth of Cultured Fibroblast Cells on Silk Protein Matrices, J. Biomed. Mater. Res. 29(10):1215-1221 (1995).
Notification of Transmittal of International Search Report and the Written Opinion of PCT/US2011/032195, mailed Oct. 27, 2011, 2 pages.
Park, I. et al., Low temperature, low pressure nanoimprinting of chitosan as a biomaterial for bionanotechnology applications, Applied Physics Letters, American Institute of Physics, 90(9):093902, 3 pages (2007).
Perry, H. et al., Nano- and Micropatterning of Optically Transparent, Mechanically Robust, Biocompatible Silk Fibroin Films, Advanced Materials, 20(16):3070-2 (2008).
Ramanujam, P.S., Optical Fabrication of Nano-Structured Biopolymer Surfaces, Opt. Mater. 27:1175-1177 (2005).
Tu, D. et al., A ZEP520-LOR Bilayer Resist Lift-Off Process by E-Beam Lithography for Nanometer Pattern Transfer, Proceedings of the 7th IEEE Conference on Nanotechnology, 624-627 (2007).
Verma, M.K. et al., Embedded Template-Assisted Fabrication of Complex Microchannels in PDMS and Design of Microfluidic Adhesive, Langmuir, 22(24)10291-10295 (2006).
Wang, L. et al., Fabrication of Polymer Photonic Crystal Superprism Structures Using Polydimethylsiloxane Soft Molds Journal of Applied Physics, 101(11):114316/1-6 (2007).
Written Opinion for PCT/US2011/032195, 5 pages (Oct. 27, 2011).
Written Opinion for PCT/US2007/083600, 5 pages (Nov. 5, 2008).
Written Opinion for PCT/US2007/083605, 9 pages (Dec. 15, 2008).
Written Opinion for PCT/US2007/083620, 5 pages (Dec. 5, 2008).
Written Opinion for PCT/US2007/083634, 5 pages (Nov. 5, 2008).
Written Opinion for PCT/US2007/083639, 5 pages (Dec. 12, 2008).
Written Opinion for PCT/US2007/083642, 5 pages (Nov. 5, 2008).
Written Opinion for PCT/US2007/083646, 9 pages (Dec. 15, 2008).
Written Opinion for PCT/US2008/082487, 9 pages (Feb. 27, 2009).
Written Opinion for PCT/US2009/047751, 4 pages (Feb. 2, 2010).
Written Opinion for PCT/US2010/022701, 4 pages (Mar. 31, 2010).
Written Opinion for PCT/US2010/024004, 5 pages (Nov. 26, 2010).
Written Opinion for PCT/US2010/042585, 5 pages (May. 25, 2011).
Written Opinion for PCT/US2010/047307, 4 pages (Apr. 28, 2011).
Xu, P. and Kaplan, D.L., Horseradish peroxidase catalyzed polymerization of tyrosine derivatives for nanoscale surface patterning, Journal of Macromolecular Science, Part A: Pure and Applied Chemistry, 41(12):1437-1445 (2004).
Yang, L.J. et al., Fabrication of SU-8 embedded microchannels with circular cross-section, International Journal of Machine Tools & Manufacturing, 44:1109-1114 (2004).

NANOIMPRINTING OF SILK FIBROIN STRUCTURES FOR BIOMEDICAL AND BIOPHOTONIC APPLICATIONS

RELATED APPLICATIONS

This application claims the benefit of priority under 35 U.S.C. 119(e) of U.S. patent application No. 61/151,866, filed Feb. 12, 2009. This patent application is a National Stage Entry of International Patent Application No. PCT/US2010/024004, which was filed on Feb. 10, 2010. This patent application also claims the benefit of priority to U.S. patent application Ser. No. 13/201,380, which was filed on Oct. 24, 2011, now U.S. Pat. No. 8,747,886. The entire contents of each of which is hereby incorporated by reference herein.

GOVERNMENT SUPPORT

This invention was made with government support under grant W911NF-07-1-0618 awarded by the United States Army. The government has certain rights in the invention.

FIELD OF THE INVENTION

The present invention is directed to nanoimprinting methods for forming nanometer-scale photonic patterns on silk fibroin-based biopolymer structures. More specifically, the invention provides for photonic nanopatterned silk fibroin-based biopolymer films, with or without a metal coating; and optical devices made thereof, including biophotonic sensors, optofluidic devices, drug delivery devices, and silk-functionalized optical fibers.

BACKGROUND OF THE INVENTION

Silk fibroin-based biopolymer films can be patterned on the micro- and nano-scale using a soft lithography techniques in which silk fibroin is cast on a photonic planar lattice. This casting process, however, takes 12 to 36 hours, which may not be convenient for rapidly producing multiple devices. In addition, although the soft lithography casting technique is effective, it may impart some artifacts to the film, such as uneven edges from mechanical lift-off or extra depth in the reproduced features from the drying process.

Nanoimprinting is an alternative high-throughput lithography technique for fabricating micro-, submicro- and nanometer-scale patterns. In this method, a mold is pressed onto a thermoplastic material heated above its glass transition temperature, and the softened material conforms to the mold due to applied pressure. There remains need for techniques to fabricate nanopatterned biopolymer films with improved resolution and high throughput, particularly at physiological and room temperatures, for use in biomedical and optical devices applications that incorporate cells, enzymes, or other heat-labile substances.

SUMMARY OF THE INVENTION

The silk photonic nanoimprinting methods of the present invention, employing hot embossing technique or ambient temperature embossing techniques, inclusive, are fast, inexpensive, and allow for a high throughput method of producing optically relevant micro-, submicro-, and nano-scale features in silk fibroin-based biopolymer films. The nanoimprinting methods, combined with the favorable optical properties of silk fibroin-based films, such as high transparency in the visible range, high mechanical stability and all aqueous processing, opens avenues for fabrication of all-organic biophotonic components on relevant milli-, micro-, submicro- and nano-scale that can be readily functionalized and employed as a new material platform. This approach seamlessly combines nanophotonics, biopolymeric and bio-compatible materials, adding a novel dimension to biomedical optical devices.

The embodiments of the present invention provide for high-throughput lithographic methods for imprinting a photonic nanopattern on a silk fibroin-based biopolymer film under a variety of conditions. More specifically, nanoimprinting of silk fibroin-based biopolymer film may be performed at elevated temperature (e.g., at ~100° C.) or at room temperature, inclusive, by locally adjusting the glass transition temperature of the silk fibroin films with different levels of hydration. The silk fibroin-based biopolymer film can also be nanoimprinted with multiple photonic patterns when repeating the imprinting processes using the same or different master patterns. Additionally, the silk fibroin-based biopolymer film can be coated with a thin metal layer before or after the imprinting process. The silk film may also be nanopatterned before or after being placed on an end of an optic fiber, functionalizing or biofunctionalizing the optic fiber. An advantage of the present invention allows for inclusion of bioactive agents, such as cells and enzymes, in the photonic patterned silk-based material.

One embodiment of the present invention relates to an imprinting method for forming a photonic nanopattern on a silk fibroin-based biopolymer film. The method comprises obtaining a silk fibroin-based biopolymer film; pressing the biopolymer film with a photonic nanopatterned substrate (i.e., a master nanopattern) at a temperature passing glass transition temperature of the biopolymer film to form a photonic nanopattern on the biopolymer film; and optionally separating the nanopattern and the nanopatterned biopolymer film.

Another embodiment of the present invention provide for an imprinting method for forming multiple nanopatterns on a silk fibroin-based biopolymer film. The method comprises the following steps: (a) obtaining a silk fibroin-based biopolymer film; pressing the biopolymer film with a first photonic nanopattern at a temperature passing glass transition temperature of the biopolymer film to form a photonic nanopattern on the biopolymer film; and separating the first nanopattern and the nanopatterned biopolymer film; (b) pressing the nanopatterned biopolymer film formed from step (a) with a second nanopattern at a temperature passing glass transition temperature of the biopolymer film, thereby forming a second nanopattern on the biopolymer film; and separating the second nanopattern and the nanopattened biopolymer film. The method may further comprise repeating step (b), thus imprinting the same silk fibroin-based biopolymer film until the desired multiple nanopattern is achieved on the biopolymer film.

In some embodiments, the silk fibroin-based biopolymer film used in the nanoimprinting method of the present invention may be coated with a metal layer before or after the imprinting process. The photonic nanoimprinting process may further include a post-imprinting step that changes the secondary structure of the silk fibroin protein from primarily random coil to primarily β-sheet structure, and increases the glass temperature and/or water-solubility of the silk fibroin.

Another embodiment of the present invention employs the nanoimprinting method of the present invention to produce a biocompatible, bioresorbable silk fibroin-based optical component can be integrated on optic fiber ends, e.g., for biomedical application. Thus, an aspect of the present invention provides for a method of functionalizing or biofunctionalizing an optical fiber. The method comprises depositing a silk fibroin-based biopolymer matrix on the endface of an optical fiber; pressing the biopolymer matrix end of the optical fiber with a photonic master nanopattern at a temperature above the glass transition temperature of the biopolymer matrix to form a photonic nanopattern on the biopolymer matrix; and separating the nanopatterned biopolymer matrix and the master nanopattern, thus producing a photonic nanopatterned silk fibroin-based biopolymer matrix on the endface of the optical fiber.

Other embodiments of the present invention relate to the use of the nanoimprinted silk fibroin-based photonic film in various applications, e.g., affixing nanoimprinted silk fibroin-based photonic film to pharmaceuticals, food products or packages; incorporating the photonic silk films in devices such surveillance devices, soft robot devices, or medical devices; incorporating nanoimprinted silk photonic structure in engineered tissues; and fabricating electro-optical devices using electroactive silk fibroin film by nanoimprinting, among other applications.

A particular advantage of the nanoimprinting method of the present invention is the ability to nanoimprint silk films at room temperature by locally reducing the glass transition temperature. This is useful for devices and applications where the silk may contain temperature-sensitive dopants or biologics such as cells, proteins and enzymes, or where the silk may be used as a nanostructured scaffold for tissue engineering.

The present invention also provides for a silk fibroin-based biopolymer film having a nanopattern thereon, fabricated using the nanoimprinting method described herein. In some embodiments, the present invention relates to an optical device that comprises such nanopatterned silk fibroin-based biopolymer film. These photonic nanopatterned silk-based films and devices may further include at least one dopant, active agent, or biologic.

BRIEF DESCRIPTION OF THE DRAWINGS

FIG. 10A presents the geometry. FIG. 10B shows periodic imprinted nanoholes 200 nm in diameter and 30 nm deep illuminated with supercontinuum. The spacings between the holes vary from right to left in the figure: 600 nm, 500 nm, 400 nm and 350 nm. In the upper panel, the medium above the holes is air. In the bottom panel, the medium above the holes is water. FIG. 10C shows wavelength versus the diffracted angle for the first four diffractive orders of the silk gratings with the periods of 400 nm (10A) and 600 nm (10B) ($n_2$=1.54, $\theta_{inc}$=80°. The shaded areas cover the parameter range observable in the experiment (within the visible spectrum frequency band and within the collection cone).

DETAILED DESCRIPTION OF THE INVENTION

Figure 1A:
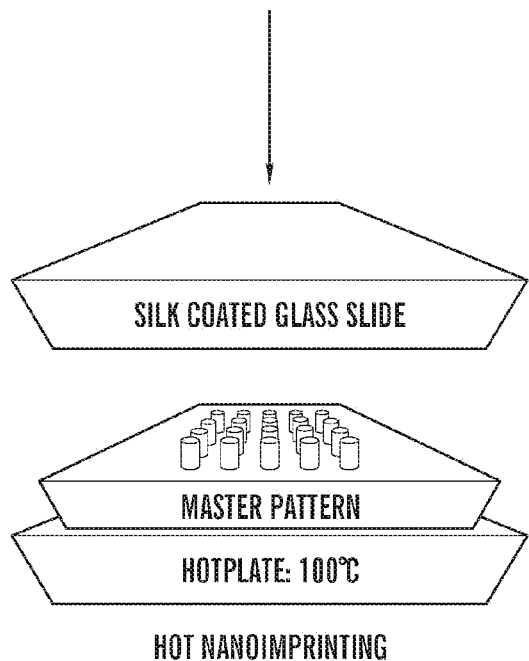
FIGS. 1A and 1B are a schematic of exemplary embodiments of nanoimprinting processes at conditions of (1A) hot embossing and (1B) room temperature embossing.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The term "nanopattern" or "nanopatterned" as used herein refers to small photonic patterning that is provided in silk fibroin-based films or optical devices comprising silk fibroin-based films, the patterning having structural features of a size that can be appropriately measured in a nanometer scale (i.e., $10^{-9}$ meters), for instance, sizes ranging from 1 nanometer to millimeters, inclusive.

Several embodiments of the nanopatterned films and the nanopatterned optical devices of the present invention are implemented herein with silk fibroin-based biopolymer, in view of its superior functional characteristics and processability. With soft micro- and nanopatterned materials becoming increasingly useful for various microfluidic, optical, mechanical, and electronic devices, the extension of this paradigm to a biopolymer-based material substrate provides new options for such devices.

Biopolymers such as silk fibroin, collagen and chitosan, are promising materials for incorporation into biomedical optical devices. Silk fibroin is a particularly appealing biopolymer candidate for forming such devices because of its optical properties (Lawrence et al., 9 Biomacromolecules 1214-20 (2008)), mechanical properties (Altman et al., 24 Biomat. 401-16 (2003); Jiang et al., 17 Adv. Funct. Mater. 2229-37 (2007)), all aqueous processing (Sofia et al., 54 J. Biomed. Mater. Res. 139-48 (2001); Perry et al., 20 Adv. Mater. 3070-72 (2008)), relatively easy functionalization (Murphy et al., 29 Biomat. 2829-38 (2008)), and biocompatibility (Santin et al., 46 J. Biomed. Mater. Res. 382-9 (1999)). For example, silk fibroin can be processed into thin, mechanically robust films with excellent surface quality and optical transparency.

As used herein, the term "silk fibroin" includes silkworm fibroin and other insect or spider silk protein (Lucas et al., 13 Adv. Protein Chem. 107-242 (1958)). Silk fibroin can be obtained from a solution containing a dissolved silkworm silk or spider silk. The silkworm silk fibroins are obtained, for example, from the cocoon of *Bombyx mori*, and the spider silk fibroins are obtained, for example, from *Nephila clavipes*. In the alternative, the silk fibroins suitable for use in the present invention can be obtained from a solution containing a genetically engineered silk harvested from bacteria, yeast, mammalian cells, transgenic animals or transgenic plants. See, e.g., WO 97/08315 and U.S. Pat. No. 5,245,012.

Silk fibroin films can be patterned on the micro- and nano-scale using a soft lithography casting technique in which silk fibroin solution is cast on a pattern and dried. See Perry et al., 2008. This casting process, however, may take 12 to 36 hours, which may not serve as a convenient method to rapidly produce multiple devices. Additionally, the resulting silk structures from the soft lithography casting technique may contain artifacts due to drying and removal processes.

Nanoimprinting is a high-throughput lithography technique of fabricating micro-, submicro- and nano-meter scale patterns. In this technique, a mold is pressed onto a thermoplastic material heated above its glass transition temperature such that the softened material conforms to the mold due to applied pressure. See Quake & Scherer, 290 Science 1536-40 (2000); Nie & Kumacheva, 7 Nat. Mater. 277 (2008); Guo, 19 Adv. Mater. 495-513 (2007). Sub-100 nm structures by nanoimprint lithography were first demonstrated in polymethylmethacrylate (PMMA) (see Chou et al., 67 Appl. Phys. Lett. 3114 (1995); Chou et al., 272 Science 85-87 (1996)), and structures as small as 10 nm are now achievable in PMMA. See Guo, 2007; Chou & Krauss, 35 Microelectron. Eng. 237-40 (1997). An ideal nanoimprint resist combines rapid imprinting times with low temperature and low pressure as well as low surface energy to aid in mold removal. As such, the mold is often coated with a low surface energy surfactant. See Beck et al., 61-62 Microelectron. Eng. 441-8 (2002). Despite these advances, nanoimprinting in biopolymers presents additional challenges because of a restricted parameter space that limits the ranges of temperature and pressures usable.

The embodiments of the present invention, however, demonstrate that silk fibroin-based photonic biopolymer films exhibit many characteristics of an ideal nanoimprinting resist, which in combination with its optical properties and biocompatibility, make it a new technology platform that seamlessly combines nanophotonics, biopolymeric and biocompatible materials.

The embodiments of the present invention provide a nanoimprinting process by which nanostructures, such as photonic lattices, can be easily and rapidly nanopatterned in seconds to minutes in silk fibroin-based films with low pressure (50 psi) and without any mold surface treatment. The nanoimprinting technique can be performed at elevated temperature (about 100° C.) or at room temperature (ambient temperature), inclusive, by adjusting the glass transition temperature of the silk fibroin-based films with different levels of hydration, and the resulting structures can reproduce features down to 50 nm or less. The nanoimprinting technique significantly increases quality and throughput compared with those achieved by other lithography techniques, such as soft lithography casting techniques. See Perry et al., 2008. In addition, the high speed and high fidelity of the silk nanoimprinting methods of the present invention, as well as the mechanical and optical properties of silk fibroin-based films, are superior to other biopolymers and biocompatible polymers such as chitosan and poly(lactic acid). See Park et al., 90 Appl. Phys. Letts. 093902-3 (2007); Christopher et al., 76A J. Biomed. Mater. Res. 781-7 (2006). Thus the silk photonic nanoimprinting techniques of the present invention have the potential to easily combine nanophotonics with biopolymeric and bio-compatible materials.

The term "master nanopattern" as used herein refers to a mold or a template possessing the desired nanopattern to be imprinted in the silk fibroin film. The master nanopattern may be a milli-micro- or nanopatterned surface and/or may be an optical device such as a nanopatterned optical grating, a lens, microlens array, beam reshaper, pattern generator, and the like, depending on the geometrical features desired in the silk fibroin film or depending on the optical features desired in the optical device comprising the silk fibroin film.

One aspect of the present invention relates to an imprinting method for forming a photonic nanopattern on a silk fibroin-based biopolymer film. The method comprises the steps of obtaining a silk fibroin-based biopolymer film;

pressing the biopolymer film with a master nanopattern at a temperature passing glass transition temperature of the biopolymer film to form a nanopattern on the biopolymer film; and, optionally, separating the master nanopattern and the nanopatterned biopolymer film.

Another aspect of the present invention relates to an imprinting method for forming multiple nanopatterns on a silk fibroin-based biopolymer film. The method comprises: (a) obtaining a silk fibroin-based biopolymer film; pressing the biopolymer film with a master nanopattern at a temperature passing glass transition temperature of the biopolymer film to form a photonic nanopattern on the biopolymer film; and separating the master nanopattern and the nanopatterned biopolymer film; (b) pressing the nanopatterned biopolymer film formed from step (a) with a second master nanopattern at a temperature passing glass transition temperature of the biopolymer film, thereby forming a second nanopattern on the biopolymer film; and, optionally, separating the second master nanopattern and the nanopattened photonic biopolymer film. The method may comprise further steps of repeating step (b), thus imprinting the same silk fibroin-based biopolymer film until the desired multiple nanopattern is achieved on the biopolymer film. Steps (a) and (b) may also be referred to as "imprinting process" or "nanoimprinting process" herein.

The master nanopatterns used in steps (a) and (b) of the imprinting method may be the same or different depending on the patterns desired. Step (b) of the imprinting method may be further repeated to generate the desired multiple nanopatterns. The alignment of the master nanopattern in step (b), with respect to the nanopattern imprinted on the silk fibroin film in the previous step, may be parallel or perpendicular or may be characterized by an orientational angle ranging from 0° to 360°, inclusive. In some embodiments, nanoimprinting of multiple patterns on silk films is achieved by repeating the imprinting process twice on the same silk fibroin film using a same master pattern or two different master patterns. In one example, the orientation of the master patterns used is 90° with respect to each other. This process and characterization of the resulting nanopatterned silk fibroin film by atomic force microscopy (AFM) are demonstrated in the Examples, below.

A silk fibroin-based biopolymer film is obtained as the imprinting resist. The silk fibroin film may be prepared by depositing an aqueous silk fibroin-containing solution on a support substrate and allowing the silk fibroin solution to dry into a film. In this regard, the substrate coated with silk fibroin-based solution may be exposed in air for a period of time, such as 12 hours. Depositing the silk fibroin solution can be performed by, e.g., using a spin coating method, where the silk fibroin solution is spin coated onto the substrate to allow the fabrication of thin membranes of non-uniform in height; or simply by pouring silk fibroin solution over the top of the substrate.

The properties of the silk fibroin film, such as thickness and content of other components, as well as optical features, may be altered based on the concentration and/or the volume of the silk fibroin solution applied to the substrate. For instance, the thickness of the silk film may be controlled by changing the concentration of the silk fibroin in the solution, or by using desired volumes of silk fibroin solution, resulting silk fibroin film with a thickness ranging from approximately 2 nm to 1 mm thick. In one embodiment, one can spin coat the silk fibroin onto a substrate to create films having thickness from about 2 nm to about 100 nm using various concentrations of silk fibroin and spinning speeds. The silk fibroin films formed herein have excellent surface quality and optical transparency.

Regarding the preparation of a silk fibroin solution, this may be done in an all-aqueous, organic manner. See U.S. application Ser. No. 11/020,650; WO 2005/012606. A micro-filtration step may be used herein. For example, the prepared silk fibroin solution may be processed further by centrifugation and syringe based micro-filtration before depositing on the substrate. This process enables the production of 8%-10% w/v silk fibroin solution of excellent quality and stability. The micro-filtration step is often desirable for the generation of high-quality optical films with maximized transparency and, consequently minimized scattering.

In addition, other biocompatible and biodegradable polymers may be blended in silk fibroin solution to form silk fibroin-based biopolymer. For example, additional biopolymers, such as chitosan, exhibit desirable mechanical properties, can be processed in water, blended with silk fibroin, and form generally clear films for optical applications. Other biopolymers, such as chitosan, collagen, gelatin, agarose, chitin, polyhydroxyalkanoates, pullan, starch (amylose amylopectin), cellulose, alginate, fibronectin, keratin, hyaluronic acid, pectin, polyaspartic acid, polylysin, pectin, dextrans, and related biopolymers, or a combination thereof, may be utilized in specific applications, and synthetic biodegradable polymers such as polyethylene oxide, polyethylene glycol, polylactic acid, polyglycolic acid, polycaprolactone, polyorthoester, polycaprolactone, polyfumarate, polyanhydrides, and related copolymers may also be selectively used. The polymer selected herein to be blended into the silk fibroin-based biopolymer should not negatively impact the controlling of the glass transition temperature of the silk fibroin-based biopolymer by varying humidity of the silk fibroin-based biopolymer.

The silk fibroin-based biopolymer film used in the nanoimprinting method of the present invention may be coated with or on a metal layer. For example, a metal layer may be coated on a silk fibroin-based biopolymer film before the imprinting process. Alternatively, the metal layer may be coated on a silk fibroin-based biopolymer that is already imprinted with a photonic nanopattern. When coating metal layers on a silk fibroin-based biopolymer film used in the nanoimprinting method, the actual sequences of coating and imprinting steps may be chosen depending on the processing condition and the anticipated applications. For example, when silk fibroin-based biopolymer films are imprinted at ambient temperature, metal layers may be coated after silk films have been imprinted. The imprinting pressure is not affected by the metal deposition, particularly when the thickness of the metal layer is below 1 μm. The glass transition temperature of the silk films is not affected by the metal deposition, and hence the imprinting temperature is not affected by the metal deposition. Repeating imprinting steps as described herein can also be applied subsequently on the metal layer coated silk fibroin-based biopolymer film, with or without pre-existing nanopatterns on the films.

Suitable metals to be used herein include, but not limited to, gold, silver, aluminum, titanium, chromium, platinum, copper, tin, indium, cadmium, lead, tungsten, iron, nickel, selenium, silicon, strontium, palladium, vanadium, zinc, zirconium, and alloys and oxides thereof. Metal can be coated on the silk film as a thin layer ranging from about 2 nm to about 10 μm, inclusive. For example, a silk film can be spin coated with a 50 nm layer of gold, and subsequently imprinted with master patterns. In one embodiment, nanoimprinting of multiple patterns is achieved by repeating the imprinting process on the same metal coated silk fibroin film, using a same master pattern or two different master patterns aligned to about 90° (or a desired orientation) with respect to each other. This process and characterization of the resulting photonic nanopatterned metal-coated silk fibroin film by AFM are demonstrated in the examples herein.

The master nanopattern used in the present invention may have the structures of photonic lattice based on periodic photonic lattices, non-periodic photonic lattices, or combinations thereof. The biophotonic structure may be a nano-textured sub-wavelength biophotonic structure. For example, suitable patterns may include periodic lattices, Fibonacci quasi-periodic lattices, Thue-Morse (TM) aperiodic lattices, Rudin-Shapiro (RS) aperiodic lattices, random lattices, and other deterministic aperiodic lattices based on number theoretic sequences. The lattices in Fibonacci quasi-periodic lattices, TM aperiodic lattices, and RS aperiodic lattices are chief examples of deterministic aperiodic lattices with increasing degrees of complexity. In particular, the R-S lattice possesses a flat spectrum of spatial frequencies (white Fourier spectrum) and can be simply thought of as the analogue of a "photonic amorphous or a fluid structure." The lattice spacing of the master pattern used in the present invention may have a broad range depending on the optical functionality desired for the imprinted silk films. For example, a periodic nanoparticle arrays with lattice spacing ranging from 20 nm to 700 nm may be used as a master nanopattern.

The nanoimprinting process of the present invention can be performed at a temperature passing the glass transition temperature of the silk fibroin-based biopolymer film. Silk fibroin films have glass transition temperatures that strongly depend on absorbed moisture. Hoagland et al., 63 J. Applied Polymer Sci. 401 (1997). For example, the silk fibroin films prepared at ambient humidity (~35%) have a glass transition temperature of about 100° C. Hence, when the silk fibroin film is prepared at a humidity greater than about 35%, an imprinting process may be employed at an elevated temperature ranging from about 20° C. to about 100° C., inclusive, by pressing a silk fibroin film against a heated master nanopattern. As another example, the glass transition temperature of silk fibroin can be done at room temperature (ambient temperature) when the silk fibroin film is water-saturated. In this regard, nanoimprinting of silk fibroin films at room temperature may require saturating the silk fibroin film, at least locally, before pressing the master nanopattern and the silk fibroin film. For example, a small drop of water may be placed on the film to achieve the water-saturated film. The different glass transition temperatures of silk fibroin are advantageous in allowing for ambient temperature nanoimprinting. Room temperature is useful particularly for devices and applications where the silk contains temperature-sensitive biological dopants such as cells, proteins and enzymes, or where the silk is used as a nanostructured scaffold for tissue engineering.

The pressure needed during the imprinting process is relatively low, for example from about 5 psi to about 50 psi, inclusive. The nanoimprinting process of the present invention is a rapid process that allows for a high throughput fabrication of multiple devices in short time. The pressing step of the imprinting process takes several seconds or minutes, inclusive. For example, the nanopattern can be formed on a silk fibroin film in a time as short as 1 second, or in less than 5 seconds, less than 1 minute or less then about 5 minutes. The pressing time may be longer at lower pressing temperatures than at higher pressing temperatures.

After imprinting, the master nanopattern may be separated easily from the resulting nanopatterned silk fibroin film, for example by levering the silk film off of the master pattern with a thin blade.

The photonic nanoimprinting process may further include a post-treatment step. The post-treatment step changes the secondary structure of the silk fibroin protein from primarily random coil to primarily β-sheet and increase the glass temperature of silk fibroin. See Hu et al., 39 Macromolecules 6161 (2006). After the post-treatments, the imprinted films are stable and last years. The post-treatment step may include water-annealing and methanol treatment. For example, the nanoimprinted silk films can be annealed in a humid environment, such as a water vapor environment, or exposed to methanol to reduce water solubility. See, e.g., Xu et al., C27 Mats. Sci. Engin. 579 (2007); Lv et al., 96 J. Appl. Polym. Sci. 2168-73 (2005); Jin et al., 15 Adv. Funct. Mater. 1241-47 (2005). The annealing time may vary, depending on the material properties desired. Typical time periods may range from a few seconds to several days, inclusive.

A particular advantage of the nanoimprinting method of the present invention is the ability to nanoimprint silk films at room temperature (ambient temperature) by locally reducing the glass transition temperature. This is complementary to the ability of silk fibroin films to maintain biological activity of dopants in the silk films, further enabling *facile* production of bioactive nanoscale devices.

Thus, in some embodiments, the silk fibroin-based biopolymer film may include at least one active agent. The agent may be embedded in the film or immobilized on the film. The variety of active agents that can be used in conjunction with the silk fibroin-based biopolymer of the present invention is vast. For example, the active agent may be a therapeutic agent or biological material, such as cells, proteins, peptides, nucleic acid analogues, nucleotides, oligonucleotides, nucleic acids (DNA, RNA, siRNA), peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, anti-inflammation agent, antifungals, antivirals, toxins, prodrugs, chemotherapeutic agents, small molecules, drugs (e.g., drugs, dyes, amino acids, vitamins, antioxidants) and combinations thereof.

Exemplary antibiotics suitable for inclusion in the photonic films of the present invention include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, or fusidic acid.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

Exemplary antibodies include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

Additional active agents to be used herein include cell growth media, such as Dulbecco's Modified Eagle Medium, fetal bovine serum, non-essential amino acids and antibiotics; growth and morphogenic factors such as fibroblast growth factor, transforming growth factors, vascular endothelial growth factor, epidermal growth factor, platelet derived growth factor, insulin-like growth factors), bone morphogenetic growth factors, bone morphogenetic-like proteins, transforming growth factors, nerve growth factors, and related proteins (growth factors are known in the art, see, e.g., Rosen & Thies, CELLULAR & MOLECULAR BASIS BONE FORMATION & REPAIR (R.G. Landes Co.); anti-angiogenic proteins such as endostatin, and other naturally derived or genetically engineered proteins; polysaccharides, glycoproteins, or lipoproteins; anti-infectives such as antibiotics and antiviral agents, chemotherapeutic agents (i.e., anticancer agents), anti-rejection agents, analgesics and analgesic combinations, anti-inflammatory agents, and steroids.

In some embodiments, the active agent may also be an organism such as a bacterium, fungus, plant or animal, or a virus. Moreover, the active agent may include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

The present invention thus provides for a silk fibroin-based biopolymer film having a photonic nanopattern thereon, fabricated using the nanoimprinting method described herein. In some embodiments, the present invention relates to an optical device that comprises such a nanopatterned silk fibroin-based biopolymer film.

The photonic nanoimprinted silk films of the present invention may reproduce fine features at sub-50 nm dimension. In one embodiment, the nanopattern on the silk films has at least one feature with a minimum dimension of about 20 nm or less. For example, characterization of a silk film nanoimprinted with periodic pattern of 200 nm diameter chromium nanoparticles (lattice constant, 250 nm) demonstrates that the smallest transverse features imprinted on silk films can be 50 nm or less. In another example, an array of nanoparticles arranged in a Rudin-Shapiro pattern was nanoimprinted on a silk fibroin film. Characterization of this aperiodic Rudin-Shapiro pattern of the silk fibroin film by AFM showed that the smallest feature reproduced was the traverse distance between the imprinted holes, measured to be 20 nm; and the cross-section analysis indicates the depth of the imprinted holes was about 30 nm.

Silk fibroin-based biopolymer film provides a favorable imprinting resist for imprinted optics compared to other biopolymers, particular when reproducing fine features at sub-50 nm dimensions. For example, when using a comparable process at a similar temperature (e.g., 90° C. and 5 psi-25 psi), chitosan-based biopolymer reproduces features of 150 nm, which is much larger than the fine feature (50 nm-20 nm or less) that silk fibroin-based biopolymer can reproduce. Moreover, chitosan does not have the high optical clarity of silk fibroin, and the nanoimprinting process takes far longer (30 min for chitosan versus a few seconds for silk fibroin). See Park et al., 2007. Furthermore, silk offers superior mechanical properties and is not subject to solubilization under acidic conditions. As another example, nanoimprinting of poly(lactic acid) (PLA), an optically clear biocompatible polymer, reproduces features down to hundreds of nanometers, which is still larger than the fine features that silk fibroin-based biopolymers as produced herein can reproduce. Moreover, PLA requires solvents in its preparation, and surface treatment of the master pattern (mold) to prevent sticking, while silk requires neither. See Christopher et al., 2006. Other room temperature nanoimprinting methods and resists exist, but require orders of magnitude more pressure than room temperature nanoimprinting of the present silk films. See Boriskina et al., 16 Opt. Express 12511-22 (2008); Khang et al., 13 Adv. Mater. 749-52 (2001).

The nanoimprintinting method of the present invention also compares favorably with the silk soft lithography casting process described previously (Perry et al., 2008). The casting process uses a similar e-beam fabricated master patterns, but although it is effective it may introduce artifacts during processing. In contrast, one of the advantages of the nanoimprinting method of the present invention is the high fidelity in reproducing fine features and improvement of the resolution of reproduced nanopatterns. For example, the nanoimprinting process described herein can reproduce 20 nm transverse features and lacks artifacts in reproducing feature depth or from liftoff. In one embodiment, the nanoimprinting process can reproduce fine features with a standard deviation within ±1 nm, ±5 nm or ±10 nm of the features of the master pattern. For example, in reproducing a 3600 grooves/mm grating with a feature depth of 75 nm in silk film by room temperature nanoimprinting method, the reproduced feature depth in silk has an accuracy of within ±5 nm of the feature depth of the master pattern. Moreover, the nanoimprinting method of the present invention requires several orders of magnitude less time when compared to the casting process, which will enable significantly larger yields in the production of nanopatterned silk devices.

The nanoimprinting method of the present invention also allows for the generation of 3-dimensional structures in the silk fibroin-based biopolymer films. For example, polycarbonate diffractive optics cards displaying a variety of 3-dimensional diffractive micro-patterns may be used as master patterns in nanoimprinting 3-dimensional structure in silk films. The surface of these master patterns are etched to encode multiple phase levels to produce fine detail and high quality projected image. Characterization of the imprinted 3-dimensional pattern on silk film by projecting images in a far field resulting from the propagation of laser through the imprinted silk optics demonstrates the capability and feasibility of creating 3-dimensional nanopatterned silk optical devices using the nanoimprinting method of the present invention.

Sophisticated optical interfaces that couple light into and out of an optical device such as a lens, microlens array, beam reshapers, pattern generators, optical gratings, and the like, may be realized in the silk fibroin-based biopolymer films using the nanoimprinting method of the present invention with the appropriated selected master nanopatterns.

One example of such optical devices is a biophotonic sensor comprising the nanoimprinted silk optics of the present invention. For example, a colorimentric biophotonic sensor described in WO 2009/061823 (made using a soft lithography casting process) can now be fabricated using the nanoimprinting method of the present invention. In addition, the ability to nanoimprint silk films at room temperature and low pressure broadens the versatility of the sensor to allow for direct incorporation and stabilization of labile biological "receptors" in the form of biologically active agents, such as antibodies, peptides, enzymes, cells, in the sensor to enable facile production of bioactive silk biophotonic sensors. For example, the biological "receptors" in the biophotonic sensor of the invention may be used to sense environmental features, such as specific active agents or chemicals, changes in active agents or chemicals, changes in pH, moisture level, redox state, metals, light, stress levels, antigen binding, prions, among other targets.

The biophotonic devices of the present invention can be readily used in environmental and life sciences where biocompatibility and biodegradability are paramount. For example, the biophotonic sensor as described above can be unobtrusively used to monitor a natural environment such as in the human body and may be implanted in vivo without a need to retrieve the device at a later time. The degradation lifetime of the biophotonic devices of the present invention can be controlled during the manufacturing process, for example, by controlling concentration, volume of the silk fibroin solution and ratio of different components in the silk solution. Moreover, the biophotonic devices of the present invention can be dispersed in the environment, again without the need to retrieve them at a later time, thereby providing novel and useful devices for sensing and detection.

Another example of the optical device is an optofluidic comprising the nanoimprinted silk optics of the present invention. Optofluidics have found emerging applications such as varieties of biological sensing and detection. Optofluidic devices were initially developed as a fusion of microfluidics and photonics to enable compact, novel optical modulation technologies. The union of optical and fluidic confining structures, however, led optofluidic devices to be applied to sensing problems (Domachuk et al., J. Opt. A-Pure Appl. Op. S129 (2007); Xiao & Mortensen, J. Opt. A-Pure Appl. Op. S463 (2007); Gersborg-Hansen & Kristensen, 15 Opt. Express 137 (2007)), particularly looking toward highly parallel, sensitive and low analyte volume applications. See Mandal et al., 6645 Nanoengin. Fabrication, Props., Optics & Devices IV J6451 (2007). Typically, optofluidic devices are fabricated from materials usually found in photonics or microfluidics such as silica, silicon, polydimethylsiloxane or polymethacrylmethacrylate and other polymers. These materials, although possessing suitable and well-characterized optical and material properties, are not inherently chemically sensitive or specific. It is possible to functionalize the surfaces of these materials with chemical reagents. See Erickson et al., 4 Microfluid. Nanofluid. 33 (2008). Nevertheless, if proteins or enzymes are used as the sensitizing agents, a much broader range of sensitivities and specificities can be achieved. The use of proteins in the traditional optofluidics, however, presents an issue in itself. Binding proteins (or chemicals receptive to them) to inorganic or synthetic polymer surfaces is complex. See Ksendzov & Lin, 30 Opt. Lett. 3344 (2005); D. Erickson & Li, 507 Anal. Chim. Acta 11 (2004).

Some embodiments of the present invention relate to development of the optofluidic paradigm, where the silk fibroin-based optofluidic device may be "activated" to be chemically sensitive and specific to species flowed past it. A material such as silk fibroin that possesses excellent optical and mechanical qualities can be formed into a variety of optofluidic geometries and maintains the activity of embedded proteins needed for realizing active optofluidic devices.

In one embodiment, a self-sensing nanoscale optofluidic device based on imprinted silk doped with lysed red blood cells was fabricated using the nanoimprinting method of the present invention. In this regard, a flow cell comprising an imprinted silk grating doped with hemoglobin was buddled with oxygen, and a light source directed through the imprinted silk grating for spectral analysis. Such optofluidic device can be thought of as "self-analyzing" in that the single optofluidic component provides both chemical and spectral analysis due to the activation of the constituent imprinted silk. The entire operation of the silk optofluidic device is enabled by the advantageous longevity of silk film and activation of protein embedded in the silk.

In another embodiment, the nanoimprinting methods of the present invention provide for a biocompatible, bioresorbable optical component can be integrated on the end of an optical fiber. Hence, aspects of the present invention provides for a method of functionalizing an optical fiber, and a functionalized optic fiber. The method comprises depositing a silk fibroin-based biopolymer matrix on the endface of an optical fiber; pressing the biopolymer matrix-end of the optical fiber with a master nanopattern at a temperature passing glass transition temperature of the biopolymer matrix to form a photonic nanopattern on the biopolymer matrix; and separating the nanopatterned biopolymer matrix from the master nanopattern, thus yielding a nanopatterned silk fibroin-based biopolymer matrix on the endface of the optical fiber.

For example, an aliquot of silk fibroin solution may be deposited on the fiber tip and the silk fibroin dried or allowed to dry. Appropriate master nanopatterns may be used to imprint optical components on the fiber's silk fibroin end. The imprinting process can be done at room temperature or by heating the fiber end using methods described herein. Optionally, a thin metal layer may be coated on the silk fibroin-based biopolymer matrix before or after the imprinting process using the nanoimprinting method as described herein. In addition, desirable multiple nanopatterns may be imprinted on the silk fibroin-based biopolymer matrix deposited on the fiber end using the nanoimprinting method as described herein. Active agents or other dopants, as described herein, may also be incorporated in this embodiment.

The nanoimprinted silk fibroin-based optical components integrated on the fiber end may also add functionality and light processing for illumination, light gathering, light splitting, light refocusing or any other modality dictated by micro- and nanopatterned surface.

In one embodiment, integration of a diffractive silk optical component on the endface of an optical fiber may be used as a way to post-process optical waveguides, allowing for improved versatility in the use of optical components in biomedical fiber optics or in any other application where rapid prototyping of the fiber tip is necessary. For example, some current optical components require cementing a small lens onto the fiber tip, resulting in exposure to liability if the fiber fails during in vivo applications, such as in catheters or endoscopic illuminators. The use of silk optical components on the tip of the fiber provides a high optical quality, sophisticated optical function with biocompatibility and biodegradability. For example, if the silk optical component on the fiber tip is detached from the fiber during in vivo use, there would be no need of removal the device due to the biodegradability of silk.

Moreover, integration of doped silk optical components into the optical fiber waveguide offers a compact way to deliver excitation source to an immobilized sample volume which conveniently overlap with the fiber propagation mode. Thus, fiber tip optics of the present invention have the ability of entraining and analyzing biomolecules with the light propagating in the fiber. Functionalizing the fiber tips with doped silks may be further used as fiber-based assays.

Additionally, a fiber tip functionalized with silk optics doped with bioactive agents opens novel avenues for drug delivery. For example, a catheter can be used to deliver one or more therapeutic agents in vivo and directly to the predefined sites that can not be readily reach by ordinarily administered pharmaceuticals. The therapeutic agents doped in the silk optics on the fiber tip may also be encapsulated in a photoactive shell, for instance, a photo-cleavable agent such as photo-cleavable biotin, and be released by directing light through the fiber to the silk optics on the fiber tip. The therapeutic agents which may be delivered via this embodiment have been described herein.

The nanoimprinted silk fibroin-based photonic film can be used in varieties of other applications. In one embodiment, the photonic silk films may be affixed to pharmaceuticals, food products or any editable novelty, or any packages. For example, the nanoimprinted silk film can be used as holographic label to provide, e.g., identification of the item being labeled. Similarly, the label itself may contain an active agent such as a pharmaceutical (e.g., an antibiotic). See, e.g., WO/2009/155397. The nanoimprinted film may be combined with other silk-based drug-delivery constructs, including microspheres, pads, porous structures, or films. See, e.g., PCT/US09/44117.

In another embodiment, the photonic silk films may be incorporated in other devices such surveillance devices, soft robot devices, or medical devices. See, e.g., PCT/US09/58534.

The nanoimprinted silk fibroin-based optical components can also used in tissue engineering. For example, nanoimprinted silk photonic structure can be affixed to engineered tissue, or the silk-based tissue-engineered construct can be used as resist of nanoimprinting. Such techniques would further confer functionality to the engineered tissues, such as monitoring the implantation or any activities of the engineered tissues in vivo.

The nanoimprinted silk fibroin-based films, with or without dopants, may also be used to fabricate electro-optical devices, such as electro-optical collectors, solar collectors, mechanical actuators with optical readout, and other applications where light-weight, degradable, electroactive devices are desired. In this regard, silk fibroin film may be modified prior to nanoimprinting. For example, through enzymatical polymerization, a conducting polymer can be generated between silk film and the substrate supporting the film, making an electroactive silk matrix. See, e.g., WO 2008/140562. Nanoimprinting of such electroactive silk matrix with photonic patterns can then generate useful electro-optical devices.

Examples

Example 1

Formation of Silk Fibroin Films

Production of silk fibroin solutions has been described previously. See Perry et al., 2008; McCarthy et al., 54 J. Biomed. Mats. Res. 139 (2001). Briefly, sericin, a water-soluble glycoprotein bound to raw fibroin filaments, was removed from the silk strands by boiling Bombyx mori cocoons in a 0.02 M aqueous solution of $NaCO_3$ for 60 min. Thereafter, the remaining silk fibroin bundle was rinsed thoroughly in purified water and allowed to dry overnight. The dry fibroin bundle was then dissolved in a 9.3 M aqueous solution of LiBr at 60° C. for 4 hr. The LiBr salt was then extracted from the solution over the course of three days, through a water-based dialysis process using Slide-A-Lyzer® 3.5K MWCO dialysis cassettes (Pierce, Rockford, Ill.). Any remaining particulates were removed through centrifugation and syringe-based micro-filtration (5 µm pore size, Millipore Inc., Bedford, Mass.). This process can yield 8%-10% (w/v) silk fibroin solution with minimal contaminants and reduced scattering for optical applications. Moreover, the silk fibroin solution may be concentrated, for example, to about 30% (w/v). See, e.g., WO 2005/012606. Briefly, the silk fibroin solution with a lower concentration may be dialyzed against a hygroscopic polymer, such as PEG, amylose or sericin, for a time period sufficient to result in a desired concentration.

Additionally, silk fibroin solution can be combined with one or more biocompatible polymers such as polyethylene oxide, polyethylene glycol, collagen, fibronectin, keratin, polyaspartic acid, polylysin, alginate, chitosan, chitin, hyaluronic acid, and the like; or one or more active agents, such as cells, enzymes, proteins, nucleic acids, antibodies and the like, as described herein. See, e.g., WO 2004/062697 and WO 2005/012606. Silk fibroin can also be chemically modified with active agents in the solution, for example through diazonium or carbodiimide coupling reactions, avidin-biodin interaction, or gene modification and the like, to alter the physical properties and functionalities of the silk protein. See, e.g., PCT/US09/64673; U.S. applications Ser. No. 61/227,254; Ser. No. 61/224,618; Ser. No. 12/192,588.

After preparation of the silk fibroin solution, 1 mL of the solution was cast on a glass microscope slide (1"×1.5") and allowed to crystallize in air overnight. The resulting film adhered to the glass slide and was approximately 20 µm-25 µm thick, depending on the concentration of the silk fibroin used. See Lawrence et al., 2008. Adjusting the concentration and/or the volume of the silk fibroin solution cast on the substrate can result in silk films from 2 nm to 1 mm thick. Alternatively, the silk fibroin solution can be spin-coated on a substrate using various concentrations and spin speeds to produce films from 2 nm to 100 µm. The silk films can also be cast on hydrophobic surfaces to make free standing films for imprinting. See Jiang et al., 2007; Lawrence et al., 2008. These silk fibroin films have excellent surface quality and optical transparency.

Additionally, the silk film may be activated, for example, by polyethylene glycol (see, e.g., PCT/US09/64673) and/or loaded with an active agent and cultured with organisms, in uniform or gradient fashion. See, e.g., WO 2004/0000915; WO 2005/123114; U.S. Patent Application Pub. No. 2007/0212730. Other addictives, such as polyethylene glycol, PEO, or glycerol, may also be loaded in the silk film to alter features of the silk film, such as morphology, stability, flexibility, and the like. See, e.g., PCT/US09/060135. More functionality may be conferred to the silk film, for example, through enzymatically polymerization a conducting polymer can be generated between silk film and the substrate supporting the film, making an electroactive silk matrix, and providing potentials of electro-optical devices after nanoimprinting. See, e.g., WO 2008/140562.

Example 2

Nanoimprinting of a Silk Fibroin Film

Silk nanoimprinting methods presented herein harness the ability to adjust the silk fibroin film glass transition temperature, which depends on the silk fibroin's absorbed moisture. See Hoagland et al., 63 J. Appl. Polymer Sci. 401 (1997). For silk fibroin films prepared at ambient humidity (~35%) the glass transition temperature is ~100° C. The glass transition temperature of silk fibroin film can be reduced to room temperature (ambient temperature) when it is water-saturated.

To nanoimprint silk films at ambient humidity, a hot embossing process was employed whereby a silk film was pressed (~50 psi) on to a heated (100° C.) master pattern for 5 sec (FIG. 1A). After imprinting, the master pattern adhered to the silk film. The master pattern was then removed easily by levering-off with a razor blade after cooling slightly (60 sec). No mold surface treatments (e.g., non-stick treatments) were necessary. For examples of films imprinted with a hot embossing technique, see FIGS. 2A, 2B, 2C, 3A, 3B, 3C, 3D, 4A, 4B, 4C, 6A, and 6B.

Figure 1B:
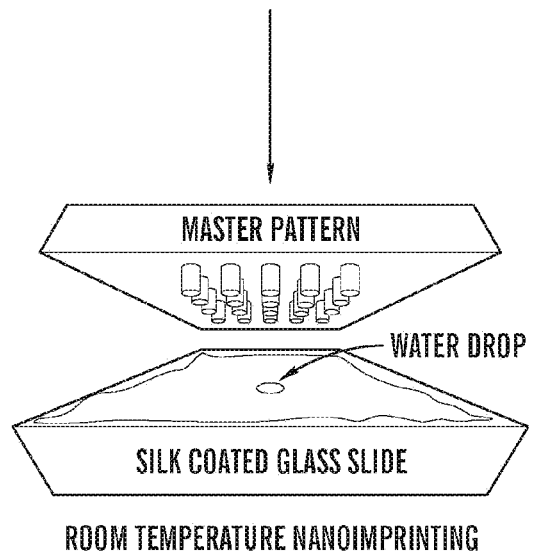

For water-saturated silk films, the glass transition temperature is ambient temperature. Nanoimprinting silk films at room temperature was achieved by depositing a small amount of water (<1 μL, e.g., a 0.5 μL drop of purified H$_2$O) on the film to locally decrease the glass transition temperature before pressing against the master pattern (FIG. 1B). The master pattern was removed easily after the film returned to ambient humidity and the excess water had evaporated (~10 min).

After imprinting, the photonic films can be annealed in a humid environment for several days, or exposed to methanol, to reduce their water solubility. These post-treatment methods change the secondary structure of the silk fibroin protein from primarily random coil to primarily β-sheet, and increase the glass temperature of silk fibroin. After the post-imprinting treatments, the optical films are quite stable and can last for years.

Additionally, the nanoimprinted silk film may also be activated, for example, through surface modification, by polyethylene glycol (See, e.g., International Application No. PCT/US09/64673), and/or loaded with an active agent or cultured with organisms in uniform or gradient fashion. See, e.g., WO 2004/0000915; WO 2005/123114; US 2007/0212730.

Example 3

Characterization of a Nanoimprinted Silk Films

To demonstrate the applicability of nanoimprinting techniques of the present invention to produce a wide variety of nanopatterned photonic silk films, several different master patterns were used for the silk film imprinting. The master patterns used herein included a 3600 groove/mm holographic diffraction grating (Edmund Optics, Inc., Barrington, N.J.), and chromium or titanium nanoparticle (200 nm in diameter and 35 nm in height) arrays arranged in periodic or Rudin-Shapiro (R-S) geometries and fabricated by electron beam lithography on silicon substrates with varying lattice constants between 700 nm and 250 nm. See Dallapiccola et al., 16 Opt. Express 5544-55 (2008); Gopinath et al., 8 Nano Lett. 2423-31 (2008). The areas of the masks range from 0.5 cm$^2$-1 cm$^2$.

Figure 2A:
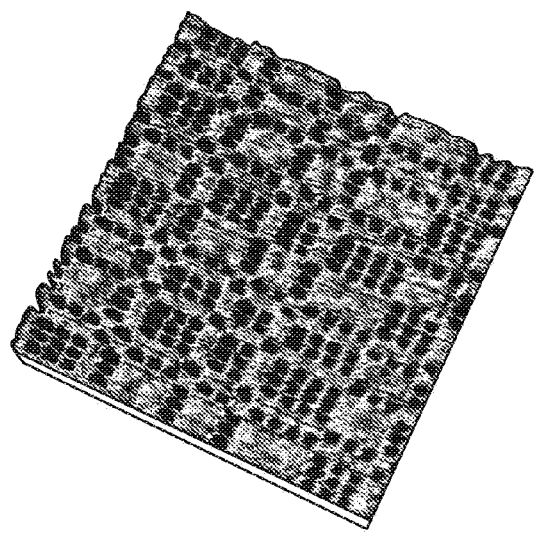
FIG. 2A shows an atomic force microscopy (AFM) image of a Rudin-Shapiro pattern imprinted in silk with 200 nm diameter holes separated by 20 nm.
Figure 2B:
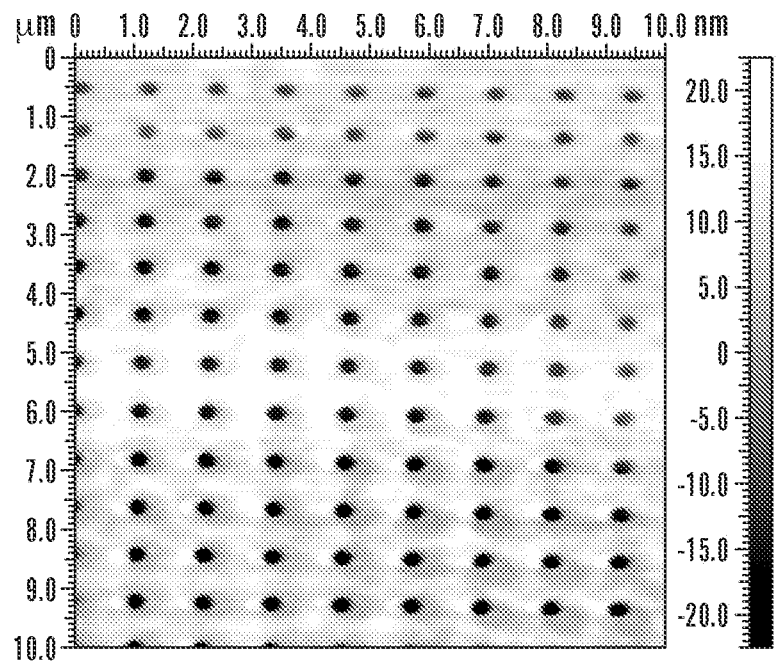
FIG. 2B is an AFM image of a periodic pattern imprinted in silk with 200 nm diameter holes separated by 400 nm.
Figure 2C:
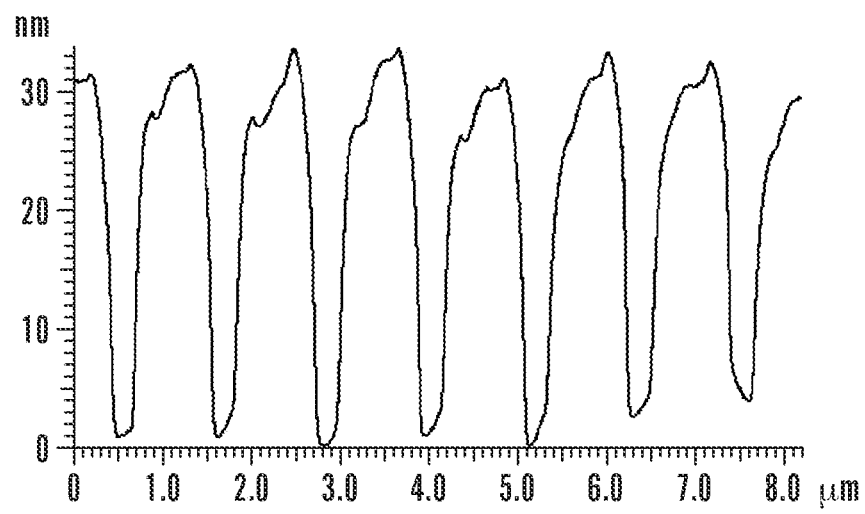
FIG. 2C represents a cross section of (2B) showing that the depth of the holes is 30 nm.

The nanoimprinted silk films were characterized with scanning electron microscopy (SEM), atomic force microscopy (AFM), and optical microscopy. The aperiodic R-S pattern nanoimprinted on the silk film is shown in FIG. 2A. From this image, the smallest feature reproduced is the transverse distance between two holes. This was measured to be 20 nm. FIG. 2B shows a nanoimprinted periodic structure. The cross-section analysis displayed in FIG. 2C indicates that the depth of the features is approximately 30 nm.

Figure 3A:
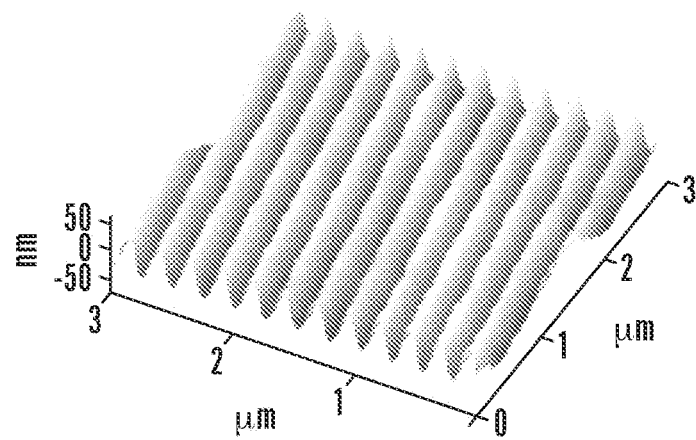
FIG. 3A is an AFM image of an imprinted silk film reproducing a 3,600 groove/mm grating.
Figure 3B:
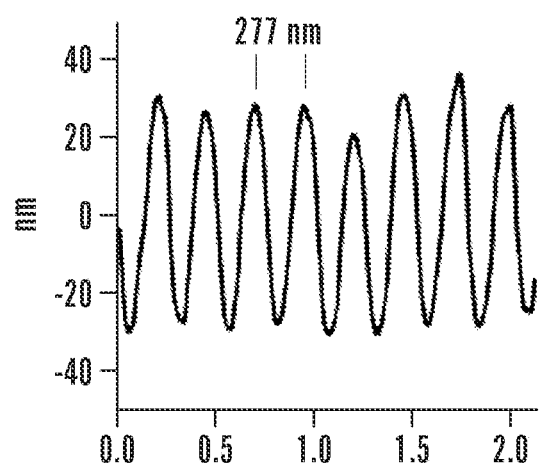
FIG. 3B represents a cross section measurement of (3A)
Figure 3C:
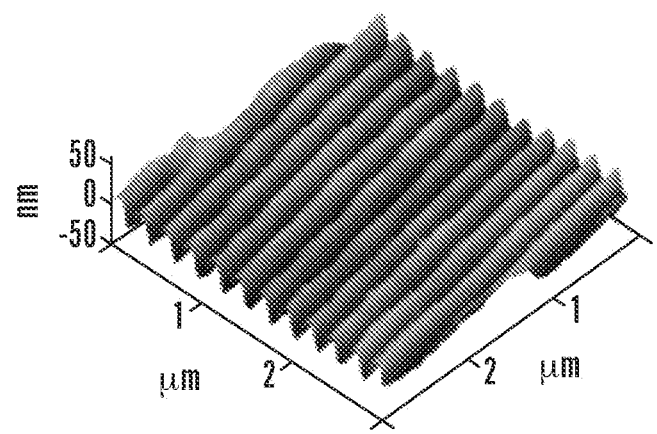
FIG. 3C is an AFM image of a master pattern used with a 3,600 groove/mm grating.
Figure 3D:
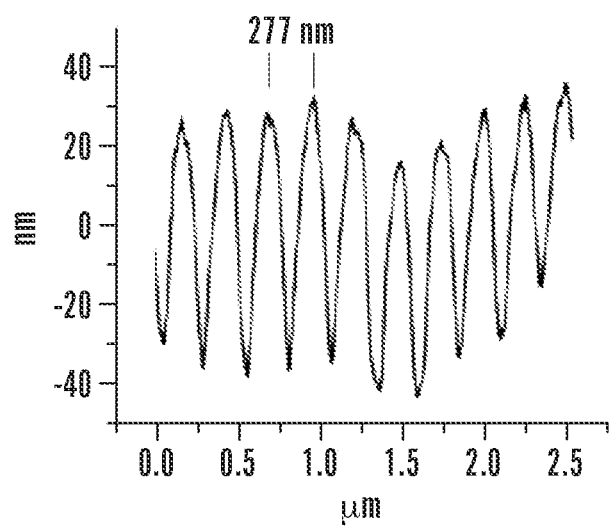
FIG. 3D represents a cross section measurement of (3C).

FIG. 3A shows a an AFM image of a 3600 grooves/mm grating imprinted at room temperature on a cast silk film. FIG. 3B shows a cross-section of the image indicating the grating period of 277 nm and a feature depth of 75 nm. FIGS. 3C and 3D show the corresponding AFM image and cross section of the master grating. A comparison of FIGS. 3A-3B and FIGS. 3C-3D demonstrates the accuracy of reproduction in the imprinted silk film using a nanoimprinting technique of the present invention.

Figure 4A:
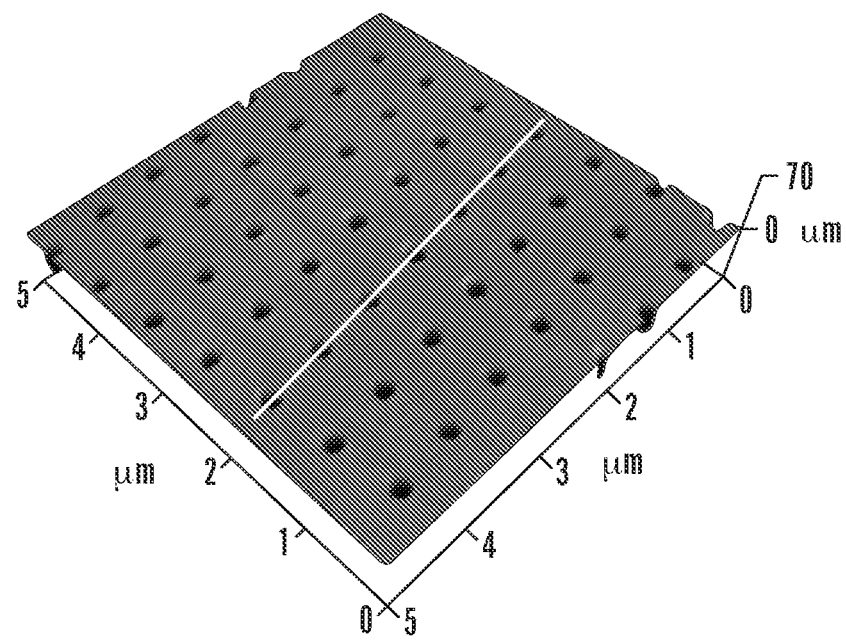
FIG. 4A is an AFM image of a periodic lattice pattern imprinted in silk with 200 nm diameter holes separated by 700 nm.
Figure 4B:
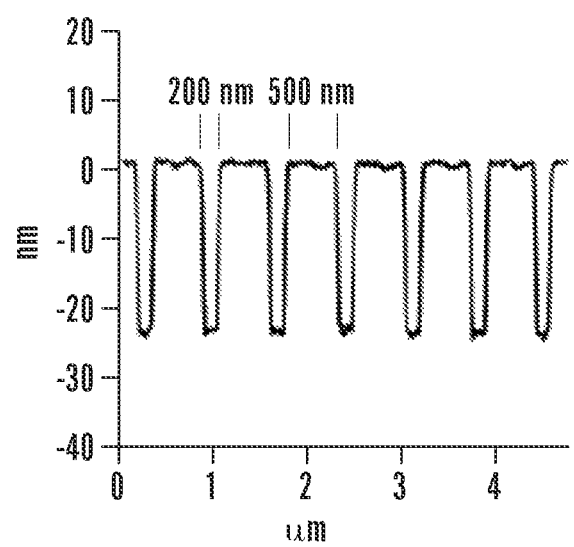
FIG. 4B represents a cross section of (4A) measured along the line illustrated in (4A)
Figure 4C:
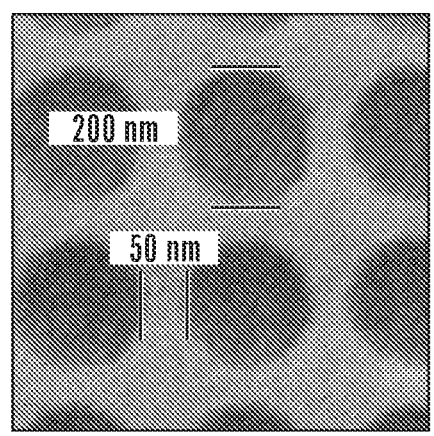
FIG. 4C is a scanning electron microscope (SEM) image of a periodic pattern imprinted in silk film with 200 nm diameter holes separated by 250 nm.

FIG. 4A is an AFM image of a silk film nanoimprinted at 100° C. with a periodic pattern of 200 nm diameter chromium nanoparticles spaced by 700 nm. FIG. 4B shows a cross section of the image in FIG. 4A. Also shown in FIG. 4C is a SEM image of a silk film nanoimprinted with a periodic pattern of similar 200 nm diameter chromium nanoparticles, but having a lattice constant of only 250 nm. This image indicates that the transverse features imprinted in silk film can be smaller than 50 nm.

Example 4

Nanoimprinting 3-Dimensional Structures in a Silk Fibroin Film

Figure 5:
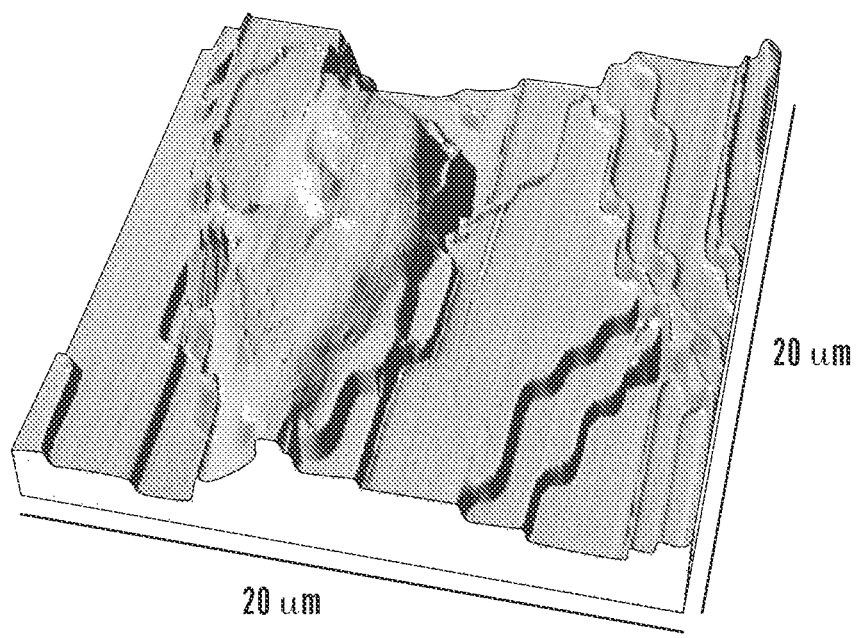
FIG. 5 is an AFM image of a 3-dimensional diffractive optic pattern imprinted in a silk fibroin film.
Figure 6A:
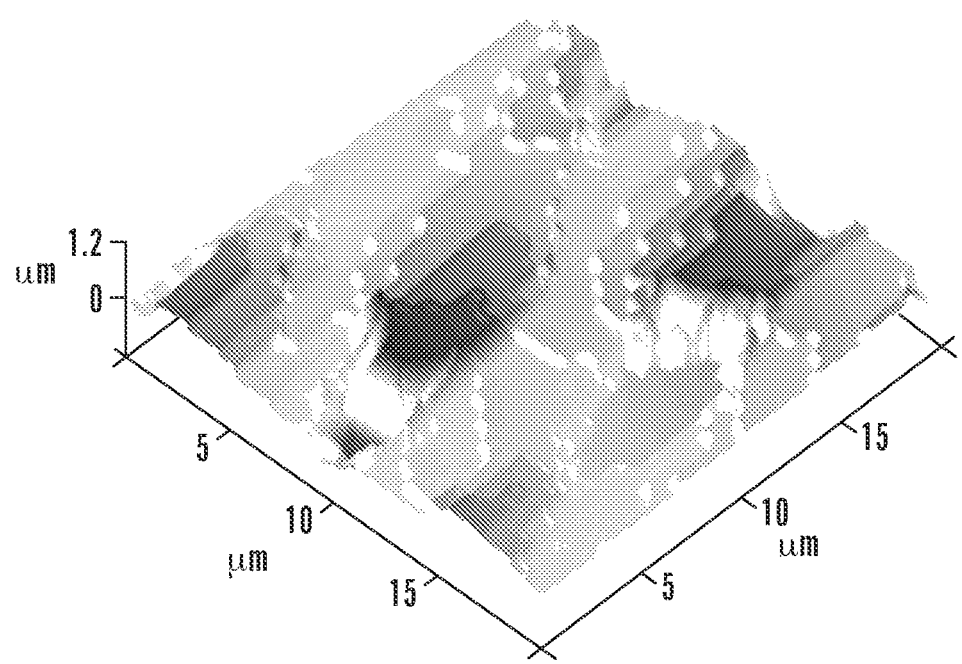
FIG. 6A is an AFM image of a 3-dimensional diffractive optic pattern imprinted in a silk fibroin film.
Figure 6B:
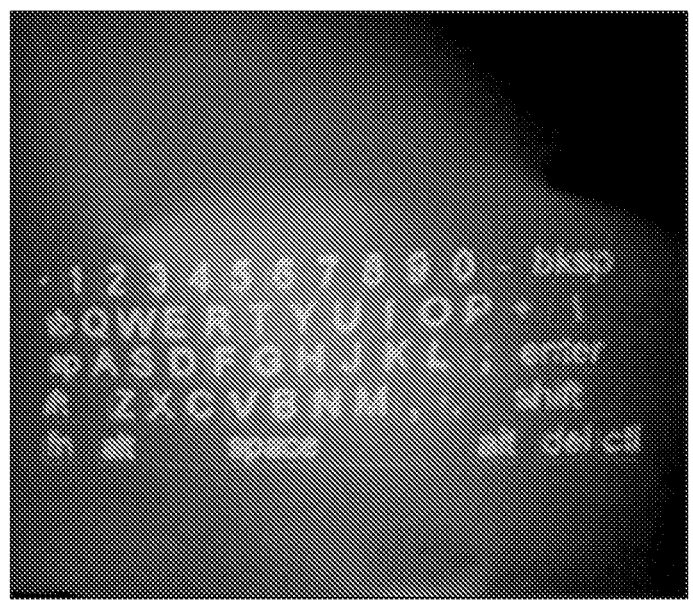
FIG. 6B is the projected due to the propagation of a He:Ne laser through the silk optic film presented in FIG. 6A. Color versions of some of the figures presented herein may be found at Amsden et al., 17 Opt. Exp. 21271-79 (2009) or Amsden et al., 22 Adv. Mater. 1-4 (2010).

Nanoimprinting of 3-dimensional structures was demonstrated using a variety of polycarbonate diffractive optics cards displaying a different 3-dimensional diffractive micropatterns (Digital Optics Corp., Charlotte, N.C.; Tessera Technologies, Inc., San Jose, Calif.). These surfaces were etched on a polycarbonate card encoded with multiple phase levels (e.g., 64 phase levels) to produce fine detail and high-quality projected images. FIG. 5 and FIG. 6A present the AFM images of imprinted 3-dimensional diffractive surface in silk fibroin films. FIG. 6B shows the projected image in the far field resulting from the propagation of a He:Ne laser through the imprinted silk optic presented in FIG. 6A. These images illustrate the 3-dimensional patterning capabilities of the nanoimprinting techniques described in the present invention, and realize silk-based optical devices.

Example 5

Nanoimprinting Multiple Nanopatterns in a Silk Fibroin Film

Figure 7A:
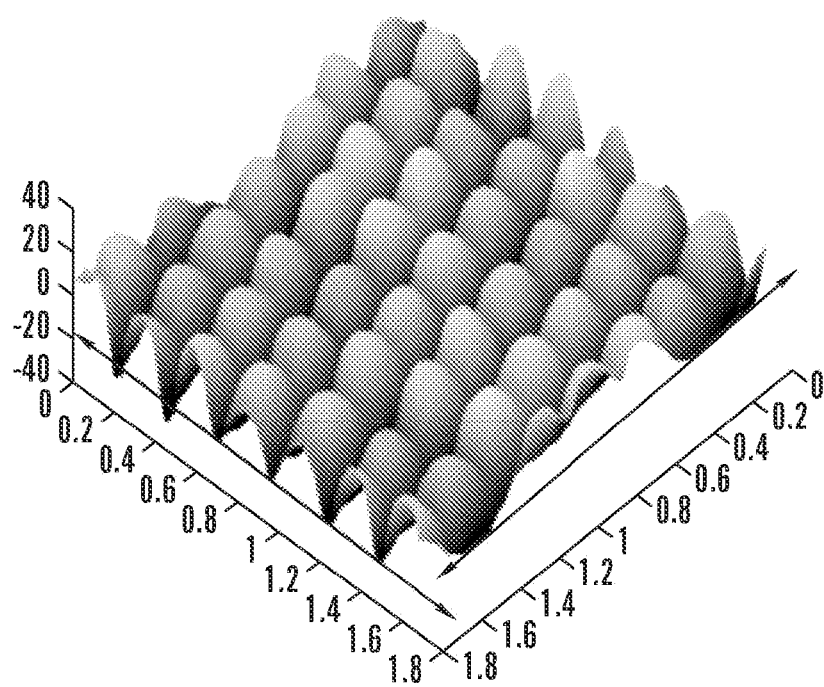
FIG. 7A is an AFM image of a 3600 groove/mm grating imprinted on a silk film twice with 90° relative orientation.
Figure 7B:
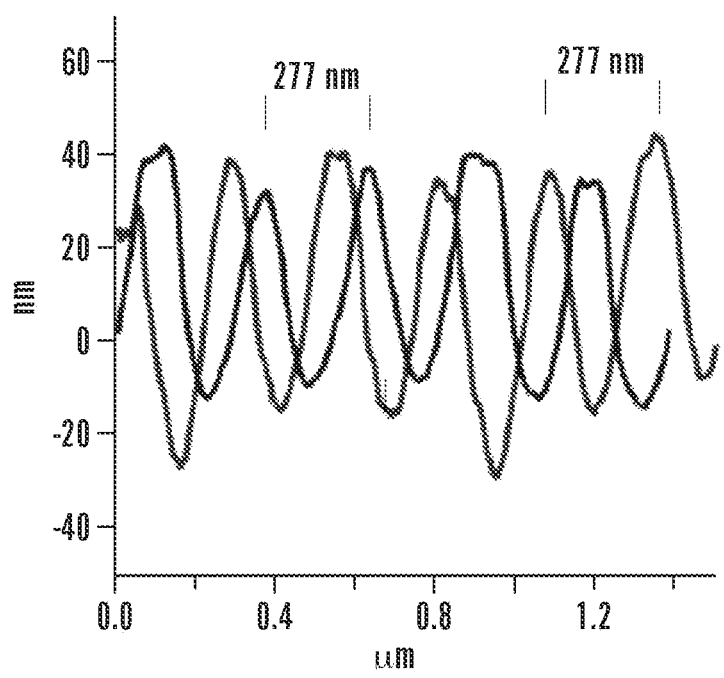
FIG. 7B is the cross section measurements along the two orthogonal directions presented in FIG. 7A.

The nanoimprinting of multiple patterns was demonstrated using sequential nanoimprinting. A 3600 groove/mm diffraction grating was used as a master nanopattern. The imprinting process was repeated twice on the same silk fibroin film with the master pattern aligned at two orientations, rotated at 90° with respect to each other. An AFM image and cross section measurements of the resulting multiple nanopatterned silk film are shown in FIGS. 7A and 7B, illustrating the ability to imprint multiple patterns on a single film. The ability to nanoimprint a film with multiple patterns is a major advantage of the nanoimprinting process described herein.

Example 6

Nanopatterns in Metal-Coated Silk Fibroin Films

The nanoimprinting of metal-coated silk fibroin films may be applied to a silk film prepared, for example, as in Example 1. This film is then coated with a thin layer of metal, such as gold. Subsequently, the nanoimprinting is accomplished with the same techniques as described herein.

Figure 8:
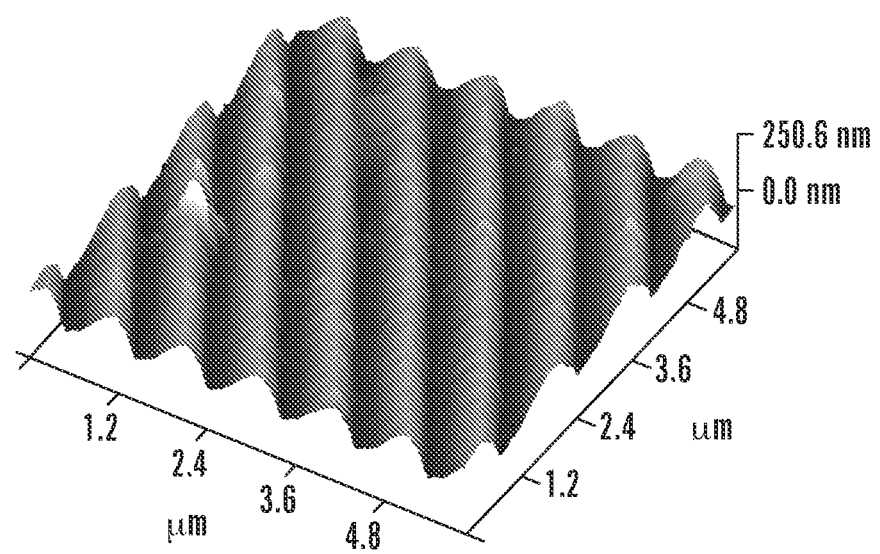
FIG. 8 is an AFM image of a 50 nm thick gold film on silk film imprinted with 1200 g/mm and 3600 g/mm gratings at 90° relative orientation.

A gold-coated photonic silk film was produced using a 1200 groove/mm grating structure and a 3600 groove/mm grating structure as master patterns. FIG. 8 shows an AFM image of a multiple nanopatterned silk film, which was coated with 50 nm of gold and imprinted by these two master patterns oriented at 90° relative to each other.

Example 7

Nanoimprinted Silk Optics as Colorimetric Sensors

Upon white light illumination, the nanoimprinted periodic structures shown in FIGS. 4A-4C behave as high-quality 2-dimensional diffraction gratings and efficiently scatter light within well-defined grating orders. The lattice constant of the imprinted structures (holes spacing) determines the scattering efficiencies of different frequencies and hence the structural color displayed. See Gopinath et al., 2008.

The microscope images and spectra in FIGS. 9A, 9B, 9C, and 10 were taken with a Nuance FX camera (CRi, Woburn, Mass.) attached to an Olympus IX71 microscope (Olympus America Inc., Center Valley, Pa.). The objective used was a 4×0.13NA Olympus UPLAN FLN objective. The illumination was from an Olympus U-DCD 0.8-0.92 NA darkfield condenser or created by nonlinear conversion of 100 fs 80 MHz laser pulses from a Spectra-Physics Tsunami® Ti:Sapphire oscillator (Newport Corp., Irvine, Calif.) in a photonic crystal fiber (19 cell 1550 nm band gap hollow core). The generated white light was transferred through a multimode optical fiber (GIF625, Thorlabs, Inc., Newton, N.J.) which was fed through a micropipette tip on an Eppendorf TransferMan® NK2 micromanipulator (Eppendorf, Hamburg, Germany). Using the micromaniupulator, the fiber was positioned 100 μm from the surface of the imprinted silk and positioned at an angle of 80° from the surface normal.

Figure 9A:
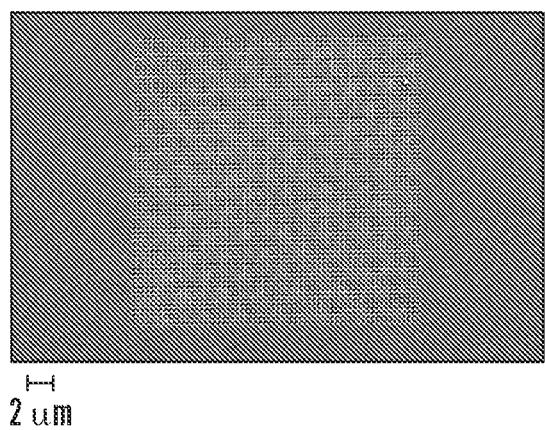
FIG. 9A shows an SEM image of periodic nanoholes in silk film. The nanoholes are 200 nm in diameter, 30 nm deep and separated by 300 nm.
Figure 9B:
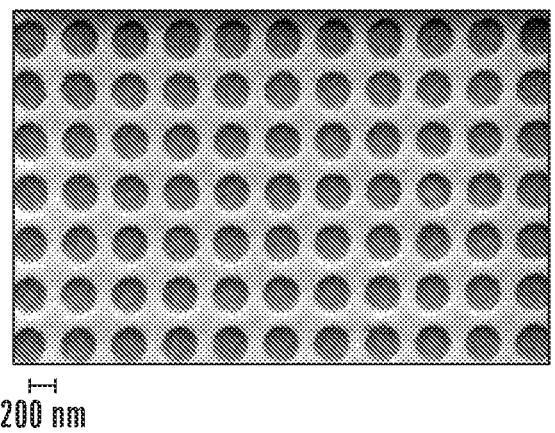
FIG. 9B shows the magnified image of FIG. 9A.
Figure 9C:
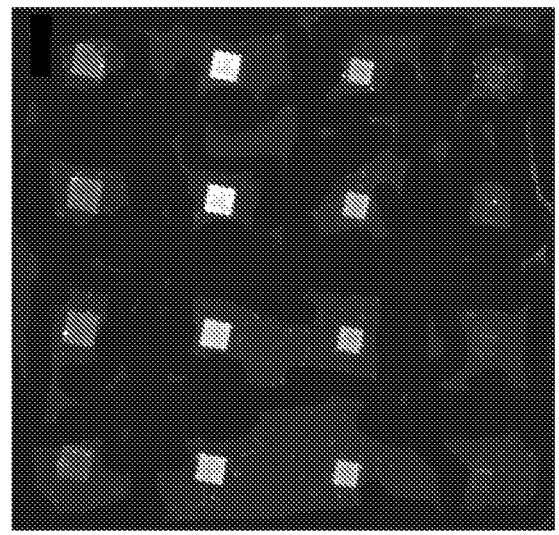
FIG. 9C presents the structural color of silk film patterned with periodic nanoholes that are illuminated with light from a dark-field condenser. The lattice constants are 700, 600, 500, and 400 nm, from left to right. The distance between the rows of colored squares is 200 µm.
Figure 10:
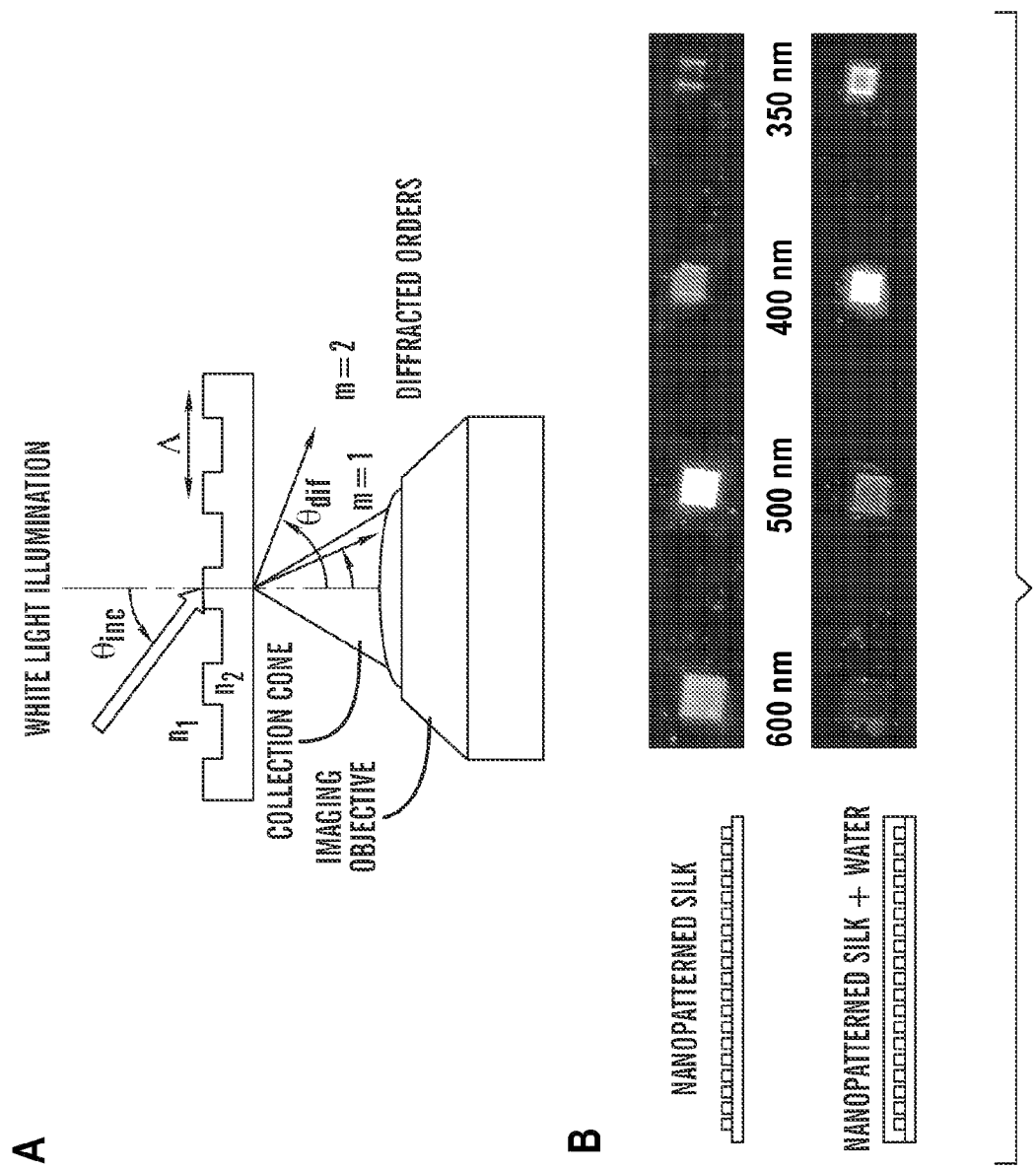
FIG. 10 presents the structural color change of nanoimprinted silk film upon immersion in water.
Figure 10:
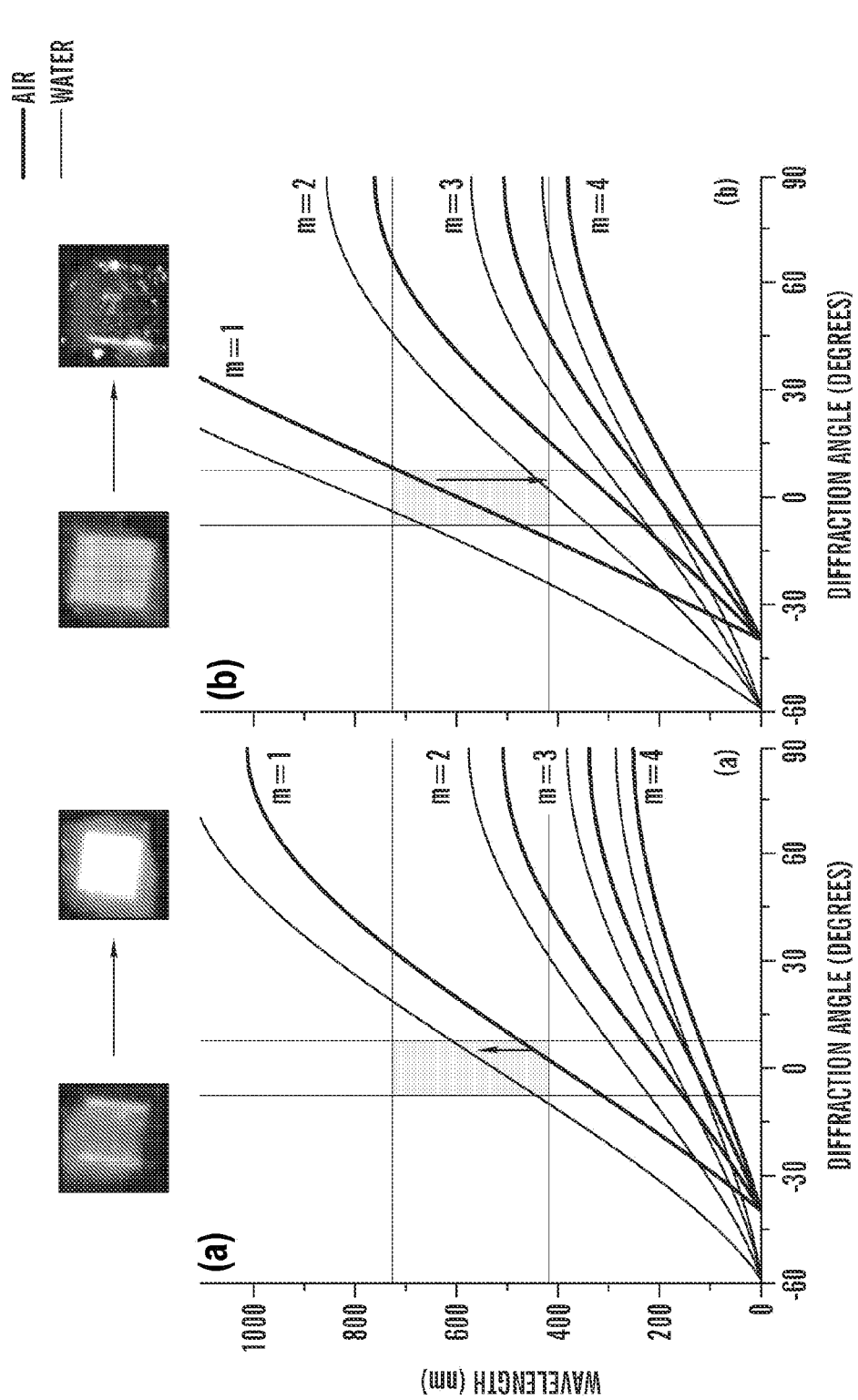

The first implementation of such structures in pure silk fibroin films is illustrated in FIG. 9, which shows planar photonic crystal lattices in periodic (FIGS. 9A and 9B) and aperiodic R-S geometries (FIGS. 9C and 9D), and the associated colors defined by their nanopatterned geometries under white light illumination.

FIG. 10B shows a 4× microscope image of the imprinted structures illuminated by supercontinuum generated in a photonic crystal fiber. The lattice constant of the structures, from left to right in the figure, are: 600 nm, 500 nm, 400 nm, and 350 nm. Upon immersion of the imprinted structures and the fiber in water, a shift in the structural color collected by the microscope objective (FIG. 10B) is demonstrated due to the change in the index of diffraction between water ($n_{water}$=1.333) and air ($n_{air}$=1.000). The mechanism of structural color change in periodically arranged air holes imprinted in transparent silk substrates can be qualitatively understood within the classical diffraction theory of periodic gratings. This equation predicts in a simple grating specific scattering angles for a given incident angle (Equation 1). See Loewen et al., Diffraction gratings and applications, (Marcel Dekker, Inc., New York, 1997).

$$\lambda = \frac{\Lambda}{m}(n_1 \sin\theta_{inc} \pm n_2 \sin\theta_{dif}), m = 0, \pm 1, \pm 2 \qquad (1)$$

$\Lambda$ is the lattice (grating) constant, $\lambda$ is the wavelengths of the incident light, $\theta_{inc}$ and $\theta_{dif}$ are the incident and diffracted angles (measured with respect to the normal to the grating surface), m is the diffraction order, and $n_1$ and $n_2$ are the refractive indices of silk and of the surrounding medium, respectively. FIG. 10A shows a schematic of the grating and the angle definitions. Because the transmitted light is collected within a small angular cone defined by the numerical aperture used in the experiments $-7.5° \leq \theta_{dif} \leq 7.5°$ (NA=0.13), only a portion of an order is collected. A change in the refractive index of the surrounding medium shifts the diffraction angles of all the grating orders, and determines the structural color response of the silk structures. This effect can be observed in FIG. 10C, where the calculated scattered wavelengths corresponding to the first four diffraction orders, the diffraction angles, and the maximum collection cone limitations are shown. Depending on the grating period and on the value of the refractive index change, two situations are possible: the same grating order is collected with a gradual red-shift in wavelength (FIG. 10B), or the successive grating order m+1, is collected as well, resulting in a blue-shift of the structural color (FIG. 10C). The observed shift in scattered color due to change in refractive index indicates that nanoimprinted silk structures are suitable candidates to engineer structural color and colorimetric sensors for solutions of different refractive indices. See Boriskina et al., 2008.

Example 8

Nanoimprinted Silk Optics as Optofluidic Devices

The utility of silk nanoimprinting for use in biophotonic sensing was demonstrated by fabricating a self-sensing optofluidic device. To make such a device, silk fibroin solution was doped with lysed red blood cells (i.e., hemoglobin) and cast on a glass slide to form a film. Using the room temperature nanoimprinting method described herein, a 600 grooves/mm grating was imprinted in the hemoglobin-doped silk film. The resulting silk optics was annealed with methanol to preserve the imprinted grating and eliminate water solubility. The doped imprinted silk grating then formed one side of a microfluidic flow cell. The remainder of the flow cell consisted of polydmethylsiloxane (PDMS) faced with a glass cover slip filled with de-ionized water. The top of the flow cell was kept open to allow for easy addition of water. A small opening was made on the bottom of the flow cell to allow for gas exchange into the cell. A tungsten light source was collimated with a 10× microscope objective and directed through the imprinted silk grating to a LC1 CCD line camera (Thorlabs, Inc.) calibrated with spectral notch filters for spectral analysis. A similarly prepared silk grating without lysed blood cells was used as a reference.

Figure 11:
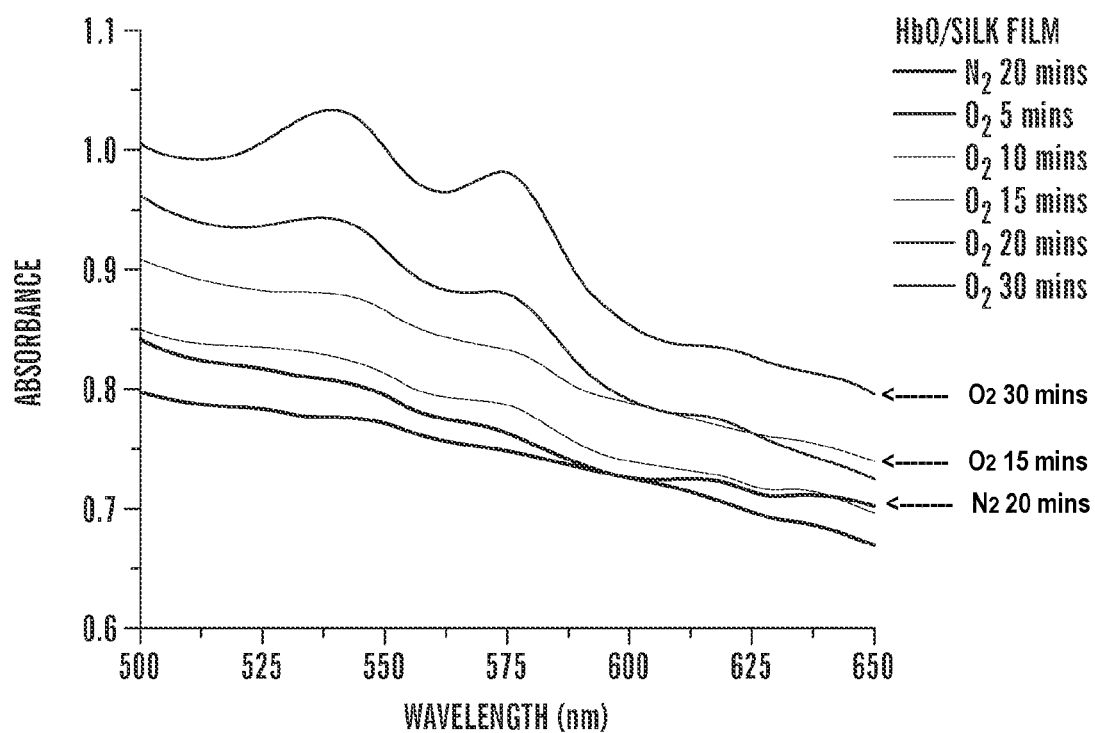
FIG. 11 is a graph showing the spectral response (absorbance versus wavelength) of a nanoimprinted silk film doped with lysed red blood cells (hemoglobin) (HbO).
Figure 12:
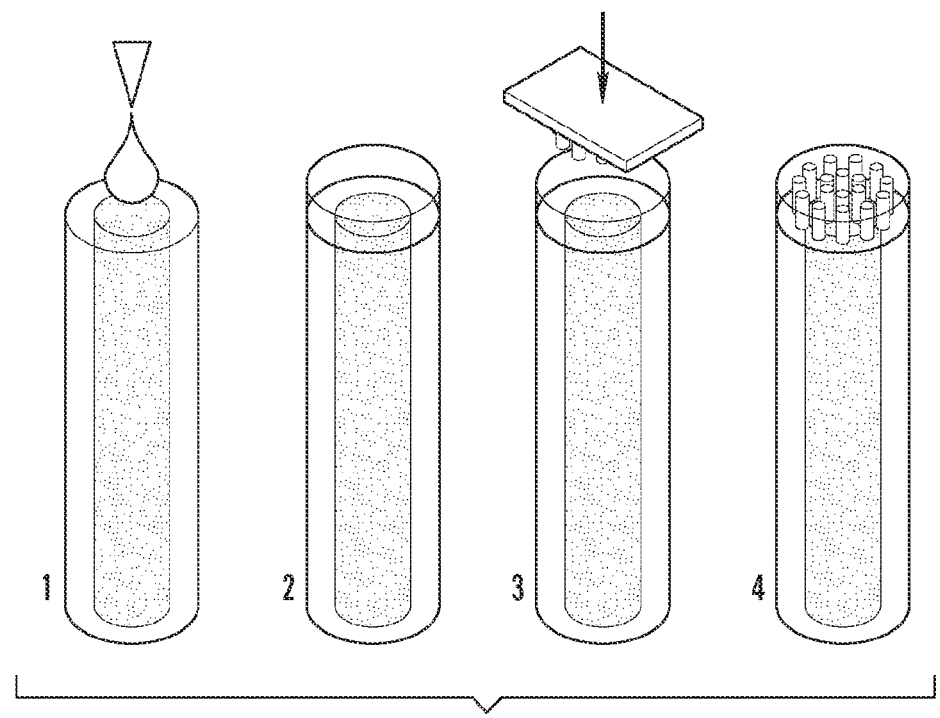
FIG. 12 is a schematic depicting the functionalization of an optical fiber end by forming a silk fibroin-based matrix on a fiber tip, then nanoimprinting the silk fibroin matrix.

FIG. 11 shows the absorption spectrum of the hemoglobin-doped, imprinted silk grating in the presence of either oxygen or nitrogen. Initially, nitrogen was bubbled through the flow cell to completely deoxygenate the hemoglobin. Upon flow of oxygen, peaks appear at 540 nm and 575 nm, indicating the binding of oxygen to the hemoglobin. The process was reversible by switching from oxygen gas to nitrogen gas. The process was also repeatable after storage of the imprinted silk film for several months. These results demonstrate the persistent activation of the hemoglobin protein inside the photonic silk matrix, despite its being subjected to the fabrication process, storage in the laboratory, and repeated experimentations. The entire operation of the silk optofluidic device is enabled by the advantageous longevity of silk film and the activation of protein embedded in the silk.

The invention claimed is:

1. A silk fibroin-based biopolymer film, comprising:
   features formed on a surface of the film and arranged in a pattern that
   (a) corresponds to a master pattern, and
   (b) substantially lacks artifacts
   wherein the patterned features include one or more transverse features with a minimum dimension of about 20 nm or less, which transverse features are reproduced relative to the master pattern with a standard deviation of ±10 nm.

2. The silk fibroin-based biopolymer film of claim 1, wherein the patterned features have at least one minimum dimension of about 50 nm or less.

3. The silk fibroin-based biopolymer film of claim 1, wherein the patterned features have at least one minimum dimension of about 20 nm or less.

4. The silk fibroin-based biopolymer film of claim 1, wherein the pattern on the surface comprises a 3-dimensional structure.

5. The silk fibroin-based biopolymer film of claim 1, wherein the pattern on the surface is a template for at least one selected from the group consisting of a lens, a microlens array, and optical grating, a pattern generator, a beam reshaper, and combinations thereof.

6. The silk fibroin-based biopolymer film of claim 1, wherein one or more active agents are embedded in or immobilized on the silk fibroin-based biopolymer film.

7. The silk fibroin-based biopolymer film of claim 1, wherein the active agents are cells, proteins, nucleic acids, antibiotics, antibodies, enzymes, or combinations thereof.

8. An optical device comprising the silk fibroin-based biopolymer film of claim 1.

9. The optical device of claim 8, wherein the optical device is a biophotonic sensor.

10. The optical device of claim 8, wherein the optical device is an optofluidic device.

11. The silk fibroin-based biopolymer film of claim 1, wherein the silk fibroin-based biopolymer film is integrated on an endface of an optical fiber.

12. The silk fibroin-based biopolymer film of claim 11, wherein the pattern on the surface forms an optical component.

13. The silk fibroin-based biopolymer film of claim 11, wherein the silk fibroin-based biopolymer film is incorporated with or functionalized with one or more bioactive agents.

14. The silk fibroin-based biopolymer film of claim 1, wherein the artifact is uneven edges in the features formed into the surface of the film.

15. The silk fibroin-based biopolymer film of claim 1, wherein the artifact is extra depth in the features formed into the surface of the film.

\* \* \* \* \*